US012582526B2

(12) United States Patent
Morelli et al.

(10) Patent No.: US 12,582,526 B2
(45) Date of Patent: Mar. 24, 2026

(54) MEDICAL IMPLANT DEVICE

(71) Applicant: Statera Medical Inc., Montreal (CA)

(72) Inventors: Moreno Morelli, Quebec (CA);
Frédérik Plourde, Quebec (CA);
Samuel Bourdon, Quebec (CA);
Thomas Ruest, Quebec (CA); Cyril Pauck-Therrien, Quebec (CA)

(73) Assignee: Statera Medical Inc., Montreal (CA)

( * ) Notice: Subject to any disclaimer, the term of this patent is extended or adjusted under 35 U.S.C. 154(b) by 600 days.

(21) Appl. No.: 17/499,409

(22) Filed: Oct. 12, 2021

(65) Prior Publication Data

US 2023/0109882 A1     Apr. 13, 2023

(51) Int. Cl.
*A61F 2/30* (2006.01)
*A61F 2/46* (2006.01)

(52) U.S. Cl.
CPC ...... *A61F 2/30* (2013.01); *A61F 2002/30525* (2013.01); *A61F 2002/3067* (2013.01); *A61F 2002/4666* (2013.01)

(58) Field of Classification Search
CPC ............. A61F 2/30; A61F 2002/30525; A61F 2002/3067; A61F 2002/4666
See application file for complete search history.

(56) References Cited

U.S. PATENT DOCUMENTS 1,388,836 A * 8/1921 Ripsch et al. ............ B66F 3/10
                                              254/102
1,547,946 A * 7/1925 Myers ....................... B66F 3/10
                                              254/102

10,492,686 B2 * 12/2019 Hunter ................... A61B 5/029
2004/0030395 A1 * 2/2004 Blunn ................ A61B 17/7016
                                              623/23.45
2004/0122440 A1 * 6/2004 Daniels ................ A61F 2/4684
                                              606/102
2007/0012491 A1 * 1/2007 Vasta ..................... A61B 17/68
                                              180/65.1
2007/0239161 A1 * 10/2007 Giger ................. A61B 17/8076
                                              606/86 A (Continued)

FOREIGN PATENT DOCUMENTS

WO     WO-2020/247890 A1     12/2020

OTHER PUBLICATIONS

International Search Report and Written Opinion for PCT Appl. No. PCT/IB2022/057775, mailed Nov. 15, 2022 (23 pages).

*Primary Examiner* — Jacqueline Woznicki
(74) *Attorney, Agent, or Firm* — Foley & Lardner LLP

(57)                ABSTRACT

Systems and methods to evaluate a joint implant device are provided. The joint implant device can include a prosthesis body having a first end and a second end. The first end can couple with a first joint component and the second end can couple with a second joint component. The prosthesis body can include a first support. The prosthesis body can include a first gear rotatably coupled with the first support. The prosthesis body can include a second support movably coupled with the first support. The second support can include a second gear that can engage with a portion of the first gear. The prosthesis body can include a third support. The third support can movably couple with the second support. The third support can move relative to the first support with activation of the first gear.

20 Claims, 14 Drawing Sheets

(56)                    References Cited

U.S. PATENT DOCUMENTS

| | | | |
|---|---|---|---|
| 2009/0112207 A1* | 4/2009 | Walker | A61B 17/707 |
| | | | 600/12 |
| 2010/0100011 A1* | 4/2010 | Roche | A61B 5/4528 |
| | | | 623/20.14 |
| 2010/0204802 A1* | 8/2010 | Wilson | A61B 5/24 |
| | | | 623/23.6 |
| 2011/0138948 A1* | 6/2011 | Jimenez | F16H 25/20 |
| | | | 74/424.82 |
| 2011/0178598 A1* | 7/2011 | Rhoda | A61F 2/4455 |
| | | | 623/17.16 |
| 2011/0251694 A1* | 10/2011 | Wasielewski | A61F 2/3859 |
| | | | 623/20.15 |
| 2013/0079668 A1* | 3/2013 | Stein | A61B 5/4585 |
| | | | 600/587 |
| 2014/0228670 A1* | 8/2014 | Justis | A61B 5/742 |
| | | | 600/409 |
| 2016/0113683 A1* | 4/2016 | Cheng | A61F 2/0811 |
| | | | 606/258 |
| 2017/0296160 A1* | 10/2017 | O'Brien | A61B 17/0206 |
| 2020/0107944 A1* | 4/2020 | Trousdale | A61F 2/4014 |
| 2021/0251665 A1* | 8/2021 | Cheng | A61B 17/72 |
| 2023/0109882 A1* | 4/2023 | Morelli | A61B 5/0002 |
| | | | 623/18.11 |
| 2024/0041617 A1* | 2/2024 | Bourdon | A61B 5/686 |
| 2025/0041074 A1* | 2/2025 | Plourde | A61F 2/482 |

* cited by examiner

105

110

205

115

105

110

410

420

415

115

MEDICAL IMPLANT DEVICE

BACKGROUND

Various medical devices can be used to support several bones, muscles, ligaments, or tendons in a body.

SUMMARY

At least one aspect is directed to a joint implant device. The joint implant device can include a prosthesis body. The prosthesis body can have a first end to couple with a first joint component and a second end to couple with a second joint component. The prosthesis body can include a first support. The prosthesis body can include a first gear rotatably coupled with the first support. The prosthesis body can include a second support movably coupled with the first support. The second support can include a second gear that can engage with a portion of the first gear. The prosthesis body can include a third support movably coupled with the second support. The prosthesis body can include the third support that can move relative to the first support with activation of the first gear.

At least one aspect is directed to a joint implant device. The joint implant device can include a body. The body can have a first end to couple with a sphere and a second end to couple with a stem. The joint implant device can include a sensor coupled with the body. The sensor can detect a physical metric proximate the first end of the body. The body can include a first support. The body can include a worm gear rotatably coupled with the first support. The body can include a second support movably coupled with the first support. The second support can include a worm wheel to engage with a portion of the worm gear. The body can include a third support movably coupled with the second support. The third support can move up to 5 centimeters relative to the first support with activation of the worm wheel.

At least one aspect is directed to a joint implant device system. The system can include a joint implant device having a sensor or an internal module. The sensor can detect a physical metric of the joint implant device. The internal module can receive a first signal from an external module to activate the internal module. The external module can be separate from the joint implant device. The external module can receive a second signal from the internal module in response to the first signal. The system can include a data processing system. The data processing system can have an input component, an adjustment component, or an output component. The input component can obtain, from the external module communicably coupled with the internal module of the joint implant device, data based on the second signal corresponding to the physical metric detected by the sensor of the joint implant device. The adjustment component can determine, based on the second signal, an indication to adjust the joint implant device.

At least one aspect is directed to a method. The method can include receiving, by an internal module of a joint implant device having a sensor, a first signal from an external module to activate the internal module. The method can include receiving, by the external module, a second signal from the internal module. The method can include obtaining, by an input component of a data processing system, data based on the second signal corresponding to a physical metric detected by the sensor of the joint implant device from the external module communicably coupled with the internal module of the joint implant device. The method can include determining, by an adjustment component of the data processing system, an indication to adjust the joint implant device based on the second signal.

These and other aspects and implementations are discussed in detail below. The foregoing information and the following detailed description include illustrative examples of various aspects and implementations, and provide an overview or framework for understanding the nature and character of the claimed aspects and implementations. The drawings provide illustration and a further understanding of the various aspects and implementations, and are incorporated in and constitute a part of this specification.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings.

DETAILED DESCRIPTION

Figure 1:
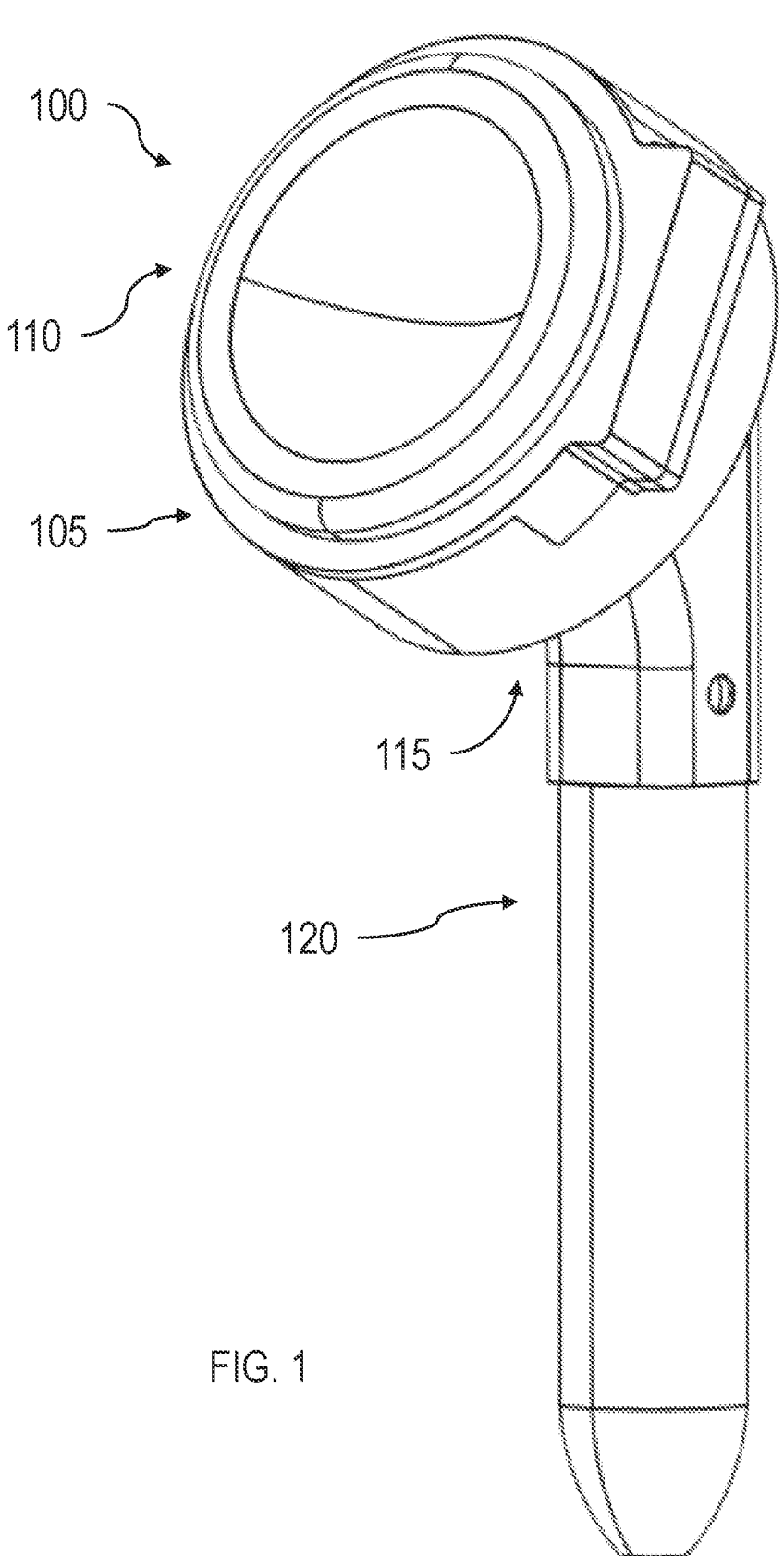
FIG. 1 is an example of a joint implant device, in accordance with an implementation.

Following below are more detailed descriptions of various concepts related to, and implementations of, methods, apparatuses, and systems of medical devices. The various concepts introduced above and discussed in greater detail below may be implemented in any of numerous ways.

The present disclosure generally refers to systems and methods for evaluating a joint implant device. The present disclosure refers generally to systems and methods of evaluating a joint implant device and determining an indication to adjust the joint implant device or maintain the position of the joint implant device. The joint implant device can be used in joint replacement operations to support or replace joints.

This technical solution is generally directed to a medical device. For example, this technical solution is generally directed to a joint implant device for coupling to a joint of a human body such as a shoulder joint, hip joint, ankle joint, elbow joint, or knee joint. Generally, joints of a human body, such as the shoulder joint, rely on soft tissues to provide an extensive range of motion with a high level of stability of the joint. When one or more portions of the joint is damaged, such as tearing of a rotator cuff, both range of motion and stability (e.g., location) of the joint may be compromised, causing instability or fracture. Various prosthesis joint replacement operations, such as a reverse shoulder replacement, can employ a medical implant device that relies on the deltoid muscle to restore shoulder functions.

During reverse shoulder replacement, anatomic shoulder replacements, or hemi arthroplasty, for example, surgeons may install a prosthesis with some tension or compression on one or more muscles, such as the deltoid muscle. To reach a desired tension, surgeons may maneuver the arm of a patient to subjectively evaluate the tension and stability of the joint (e.g., via patient feedback), which can be time consuming or ineffective. Additionally, post-operative complications, such as scapula fractures, dislocations, and limited range of motion, are linked to an inadequate tension in the deltoid muscle. Furthermore, many prosthesis devices are limited by a fixed thickness and can only be modified during arthroplasty. Therefore, there is a need to provide surgeons with objective data of the stability of the joint and intensity of force (e.g., static or dynamic force on the prosthesis) in the joint to subsequently incrementally adjust the prosthesis with a simple action of a hand tool.

This technical solution provides an adjustable prosthesis and user interface to provide surgeons with objective data regarding an orientation and amplitude of force on the prosthesis. Furthermore, if the orientation or level of force is not adequate, the prosthesis can be continuously adjusted with a simple action such as turning a hand tool. This technical solution also provides post-operatively measuring data and adjusting the prosthesis with a minimally invasive procedure or non-invasive procedure, reducing discomfort and risk for the patient.

Further, this technical solution may have many benefits over existing medical device evaluating systems. For example, by determining objective data measurements using various computing devices, the technical solution may provide more precise physical metrics of a medical device in comparison to manual evaluation techniques. Furthermore, since typically known evaluation and adjustment techniques are typically generated manually, such adjustments are often derived based on subjective data on a case-by-case and practitioner-by practitioner basis. This technical solution provides for repeatable and accurate evaluation outcomes to more efficiently and effectively adjust a medical device to meet patient needs. Various other technical benefits and advantages are described in greater detail herein.

Figure 2:
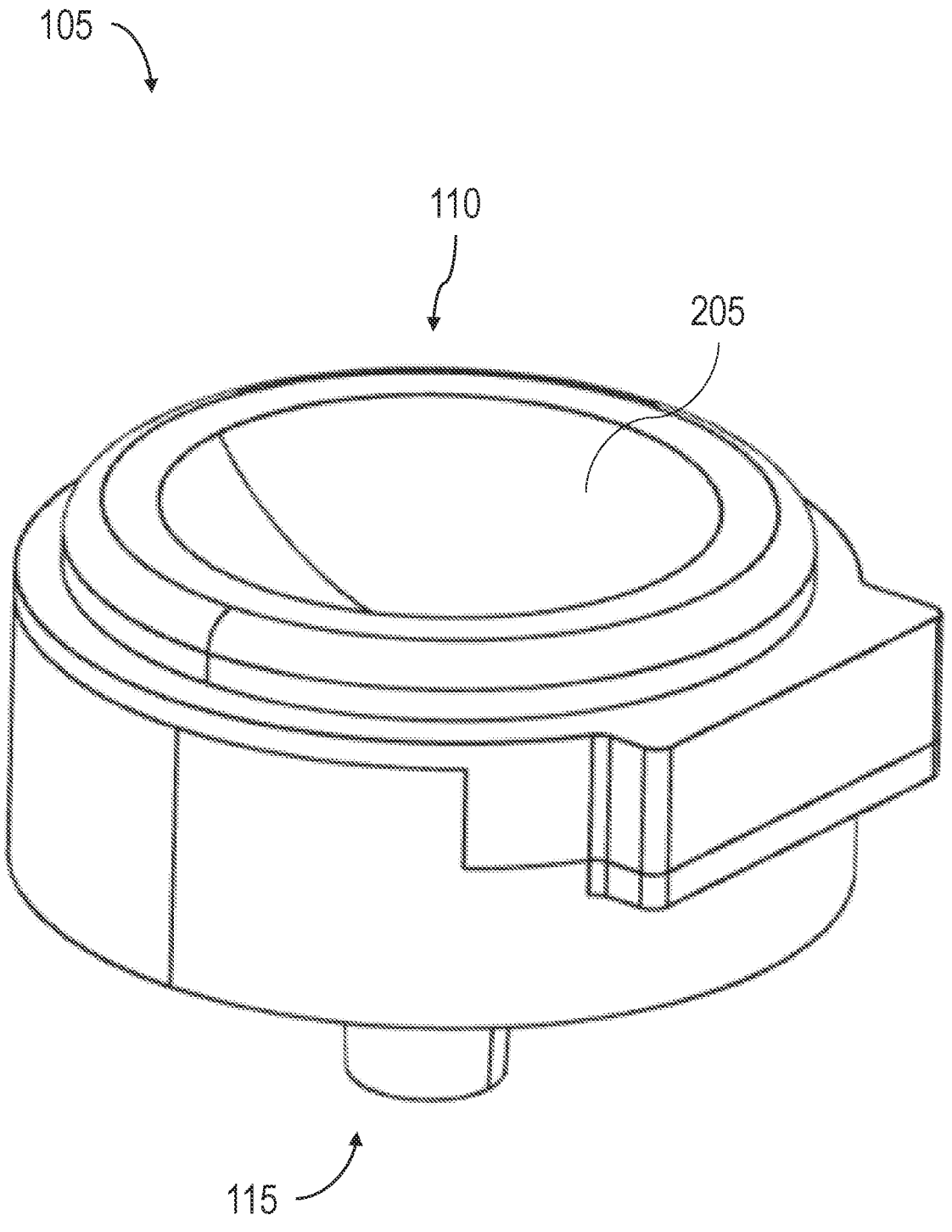
FIG. 2 is a top perspective view of a portion of the joint implant device of FIG. 1, in accordance with an implementation.
Figure 3:
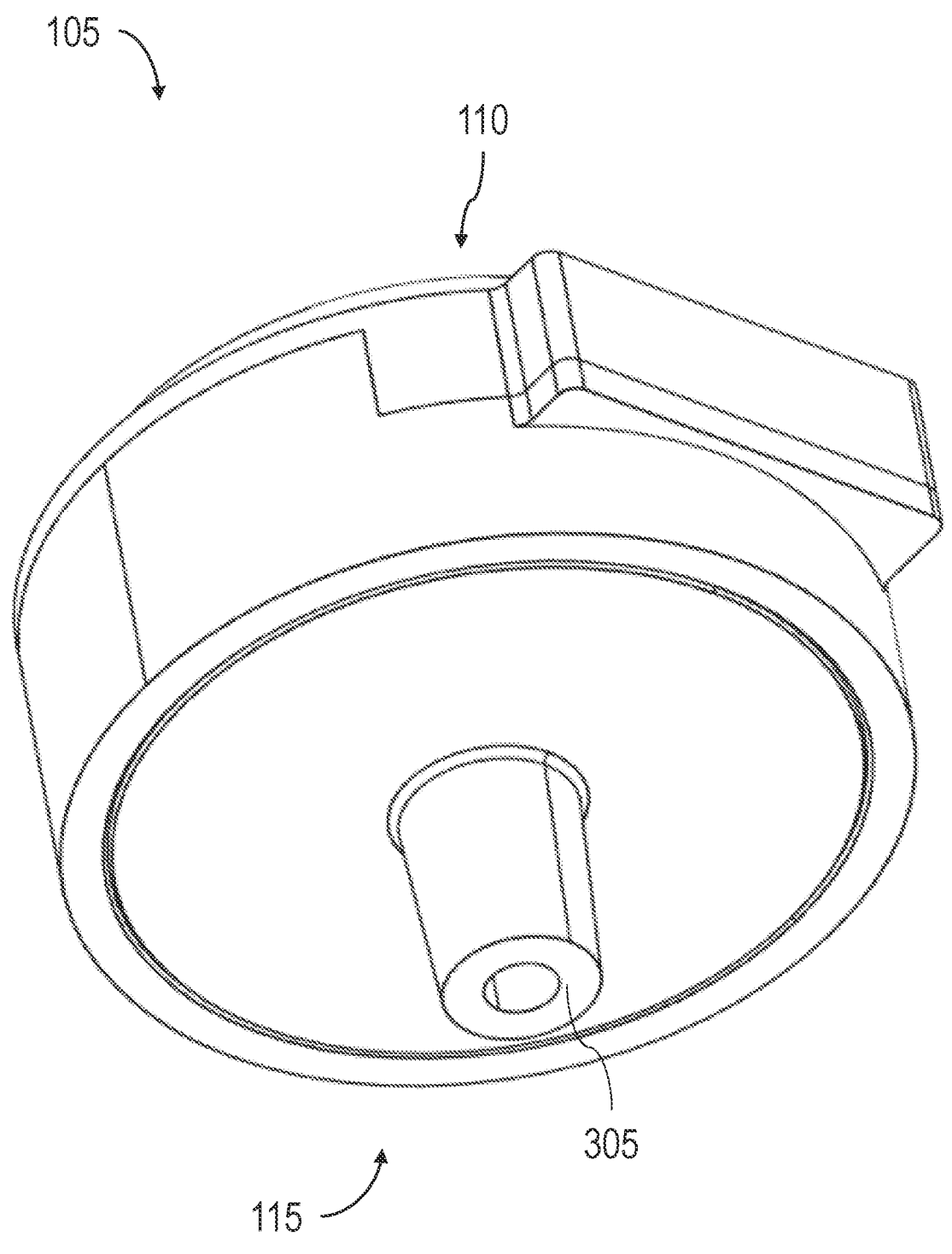
FIG. 3 is a bottom perspective view of a portion of the joint implant device of FIG. 1, in accordance with an implementation.

FIG. 1 illustrates an example joint implant device 100. For example, the joint implant device 100 can couple with various joints in a body such as a shoulder joint, a hip joint, an ankle joint, a knee joint, a wrist joint, an elbow joint, or another joint. While the joint implant device 100 described in reference to the figures generally relates to a shoulder joint, the joint implant device 100 can be used with various other joints. The joint implant device 100 can include at least one body 105, as shown in FIGS. 2 and 3, and among others. For example, the body 105 can include a prosthesis body (e.g., an artificial body part). The body 105 can include at least one component. The body 105 can be made from various metallic or non-metallic materials including, but not limited to, chromium. nickel, stainless steels, titanium, plastics, polyethylene, such as ultra-high-molecular-weight polyethylene, or ceramics. The body 105 can include a first end. For example, the first end 110 can couple to a first joint component, such as a glenoid sphere (not shown in the figures). The first end 110 can include one or more surfaces to receive a portion of the glenoid sphere. For example, the first end 110 can include at least one curved, cratered, or annular surface 205 to receive a portion of the first joint component, as described in greater detail below. In some examples, the first end 110 can couple to various other joint components including, but not limited to, a humeral component or stem, femoral component or pelvic component.

The body 105 can include a second end 115. For example, the second end 115 can couple to a second joint component, such as a humeral stem 120. The second end 115 can include an attachment projection 305 to couple with a portion of the second joint component, as shown in at least FIG. 3. For example, the attachment projection 305 can include a taper, hole, slot, aperture, or other similar opening for receiving a portion of the second joint component. In some examples, the second end 115 can couple to various other joint components including, but not limited to, a glenoid sphere or component, tibia component or a femoral component. In some examples, the second end 115 can oppose the first end 110, as shown throughout the figures. In some examples, the body 105 extends longitudinally between the first end 110 and the second end 115 along a longitudinal axis. In some examples, the body 105 may include an arcuate or angled shape such that the first end 110 and the second end 115 are disposed at an angle. In some examples, the first end 110 can couple with the second joint component and the second end 115 can couple with the first joint component (e.g., the first end 110 and the second end 115 may be interchangeable depending on the application).

Figure 4:
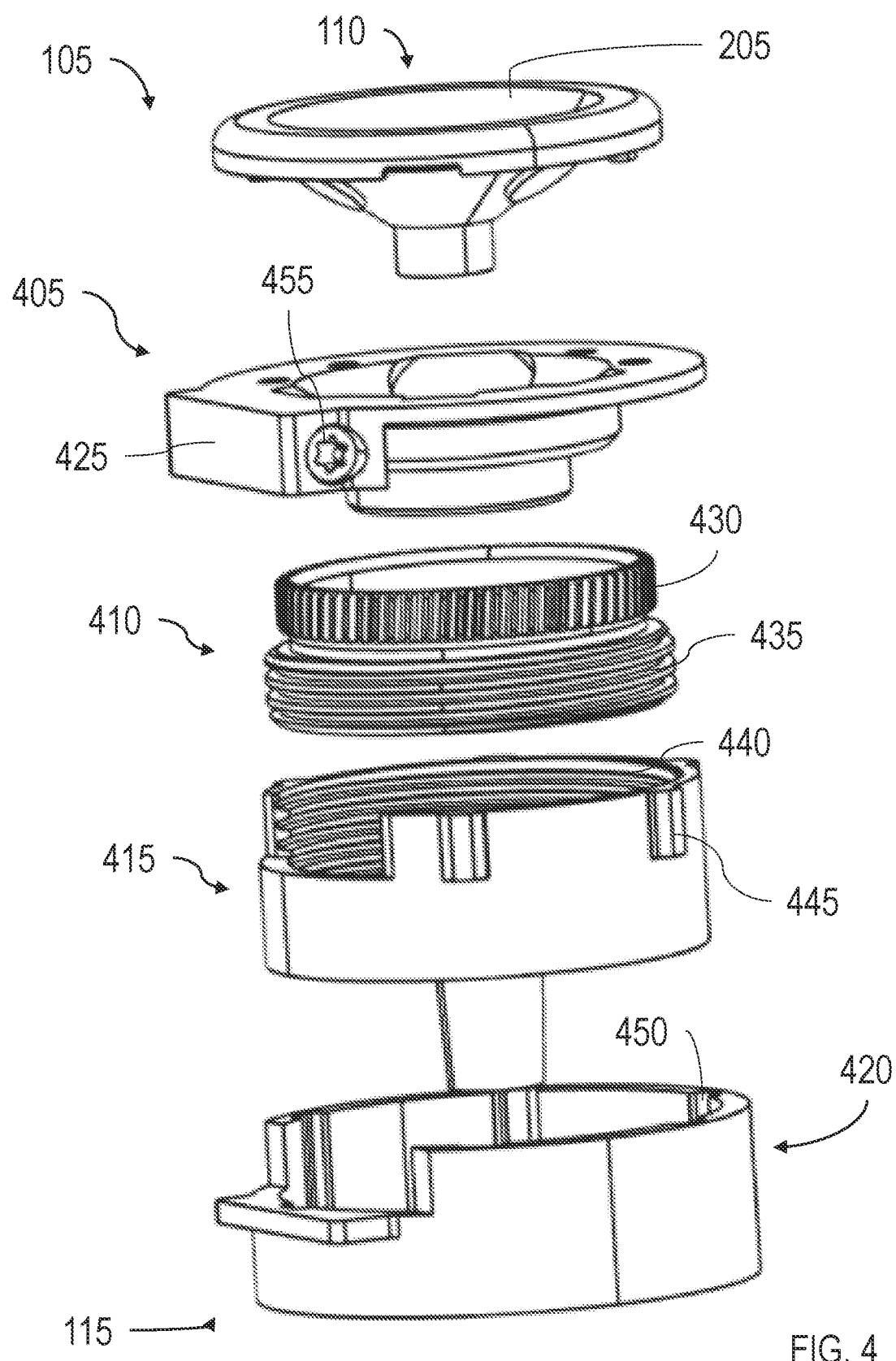
FIG. 4 is an exploded perspective view of a portion of the joint implant device of FIG. 1, in accordance with an implementation.

FIG. 4 illustrates a perspective exploded view of a portion of the body 105 of the joint implant device 100. The body 105 can include at least one support that makes up the body 105. For example, the body 105 can include a first support 405. The first support 405 can couple with a portion of the annular surface 205 that receives a portion of the first joint component, as an example. In some examples, the first support 405 corresponds in shape with the body 105 (e.g., has a cylindrical shape in length along central axis, a spherical cross-section, etc.). In some examples, the first support 405 may not correspond in shape with the body 105.

The body 105 can include a first gear 505 (shown in at least FIG. 5) rotatably coupled with a portion of the body 105, such as the first support 405. For example, the first support 405 can include a slot, hole, aperture, or other similar component to receive the first gear 505. In some examples, a portion of the first support 405 can include an extension 425 to at least partially surround or enclose a portion of the first gear 505 such that the first gear 505 is not exposed to an exterior portion of the body 105. In some examples, the first gear 505 is a worm gear. In some examples, the first gear 505 may be another gear, such as a pinion, bevel gear, screw gear, helical gear, or the like.

The first gear 505 can rotate relative to the first support 405. For example, the first gear 505 can movably couple with the first support 405 such that the first gear 505 can rotate relative to the first support 405 even when the first support 405 is stationary. In some examples, the first support 405 includes a rod, shaft, axle, or other similar component to facilitate rotatably coupling the first gear 505 with the first support 405. In some examples, the first support 405 includes a bushing or bearing to facilitate rotatably coupling the first gear 505 with the first support 405.

The body 105 can include a second support 410 movably coupled with another portion of the body 105, such as the first support 405. For example, the second support 410 can rotate or move axially (e.g., between the first end 110 and the second end 115) relative to the first support 405. The second support 410 can include a second gear 430 to engage with the first gear 505. For example, the second gear 430 can couple with or integrally form with one or more portions of the second support 410. In some examples, the second gear 430 forms a portion of the second support 410, as shown throughout the figures. For example, the second gear 430 and the second support 410 may form one unitary structure. The second gear 430 can be a worm wheel to engage with the first gear 505. The second gear 430 can include various other types of gears including, but not limited to, a bevel gear, rack, helical hear, screw gear, or the like.

The body 105 can include a third support 415 movably coupled with the second support 410. For example, the third support 415 can include a first plurality of corrugations 440 (e.g., threads) positioned along an outer portion of the third support 415 to engage with a second plurality of corrugations 435 positioned on an outer portion of the second support 410. The first plurality of corrugations 440 can rotatably engage with the second plurality of corrugations 435 such that the third support 415 can move axially relative to the second support 410 upon rotation of the second support 410. For example, the body 105 can include at least one feature to prevent rotation of the third support 415 relative to the second support 410 such that rotation of the second support 410 causes the third support 415 to move axially between the first end 110 and the second end 115 of the body 105 as the second plurality of corrugations 435 align with and create force against the first plurality of corrugations 440.

The body 105 can include a fourth support 420 coupled with the third support 415. The fourth support 420 can movably couple with a first portion of the body 105, such as the third support 415. The fourth support 420 can rigidly couple with a second portion of the body 105, such as the first support 405. For example, the fourth support 420 can include at least one alignment slot 450 coupled with or formed with the fourth support 420 to movably receive a portion of the third support 415, such as an alignment projection 445 coupled with or formed with the third support 415. The alignment projection 445 can move within the alignment slot 450 as the third support 415 moves, for example. The alignment slot 450 can include a slot disposed on an inner portion of the fourth support 420 and the alignment projection can include a projection disposed on the third support 415 to facilitate preventing rotation of the third support 415 relative to the fourth support 420. For example, the alignment projection 445 can fit within a portion of the alignment slot 450 such that the alignment projection 445 can move in an axial direction without rotating. The fourth support 420 can include one or more components to rigidly couple with the first support 405 (e.g., such that the fourth support 420 does not move relative to the first support 405). For example, the first support 405 and the fourth support 420 can couple through various means including, but not limited to, fasteners, welding, adhesives, or other similar techniques.

The third support 415 can move relative to the first support 405 with activation of the first gear 505. For example, when the first gear 505 is rotated, the rotation of the first gear 505 can cause the second gear 430 to rotate, which causes the second support 410 to rotate. As the second support 410 rotates, the second plurality of corrugations 435 can engage with the first plurality of corrugations 440 which can cause the third support 415 to move axially relative to the second support 410. For example, the force of the alignment projection 445 against the alignment slot 450 preventing rotation can cause the third support 415 to move axially as each of the plurality of corrugations align with and engage with one another.

In some examples, the first plurality of corrugations 440 can extend longitudinally along the third support 415 a greater distance than the second plurality of corrugations 435 extend longitudinally along the second support 410. For example, if the second plurality of corrugations 435 extends about 1 centimeter longitudinally between the first end 110 and the second end 115 of the body 105 along the second support 410, the first plurality of corrugations 440 may extend about 1.5 centimeters longitudinally between the first end 110 and the second end 115 of the body 105 along the third support 415. These measurements are for illustrative purposes only and are not limiting to the scope of the present disclosure. Each of the plurality of corrugations may extend significantly longer or short distances along each respective support.

The joint implant device 100 can include at least one actuator 455 operably coupled with a portion of the first gear 505. For example, the actuator 455 can include a fastener to engage with a portion of the first gear 505. In some examples, the actuator 455 can receive a portion of a hand tool (e.g., screw driver, wrench) to facilitate actuating (e.g., rotating) the first gear 505 relative to the first support 405. For example, the first gear 505 can slidably receive a portion of the actuator 455 such that rotation of the actuator 455 causes rotation of the first gear 505 relative to the first support 405. In some examples, the actuator 455 includes a rod, axle, or other similar component to facilitate rotatably coupling the first gear 505 with the first support 405. In some examples, the actuator 455 can automatically actuate via one or more components of a data processing system or device application, as will be described in greater detail below. For example, one or more signals from a control system (e.g., data processing system described below) can cause the actuator 455 to rotate a specific amount.

Each of the supports of the body 105 (e.g., the first support 405, the second support 410, the third support 415, and the fourth support 420) can be made from various metallic or non-metallic materials. For example, each support may be made from stainless steel, titanium, copper, or the like. Each support may be made from plastic, resin, rubber, or the like. Each support may be made from a combination of metallic and non-metallic materials, as another example.

Figure 5:
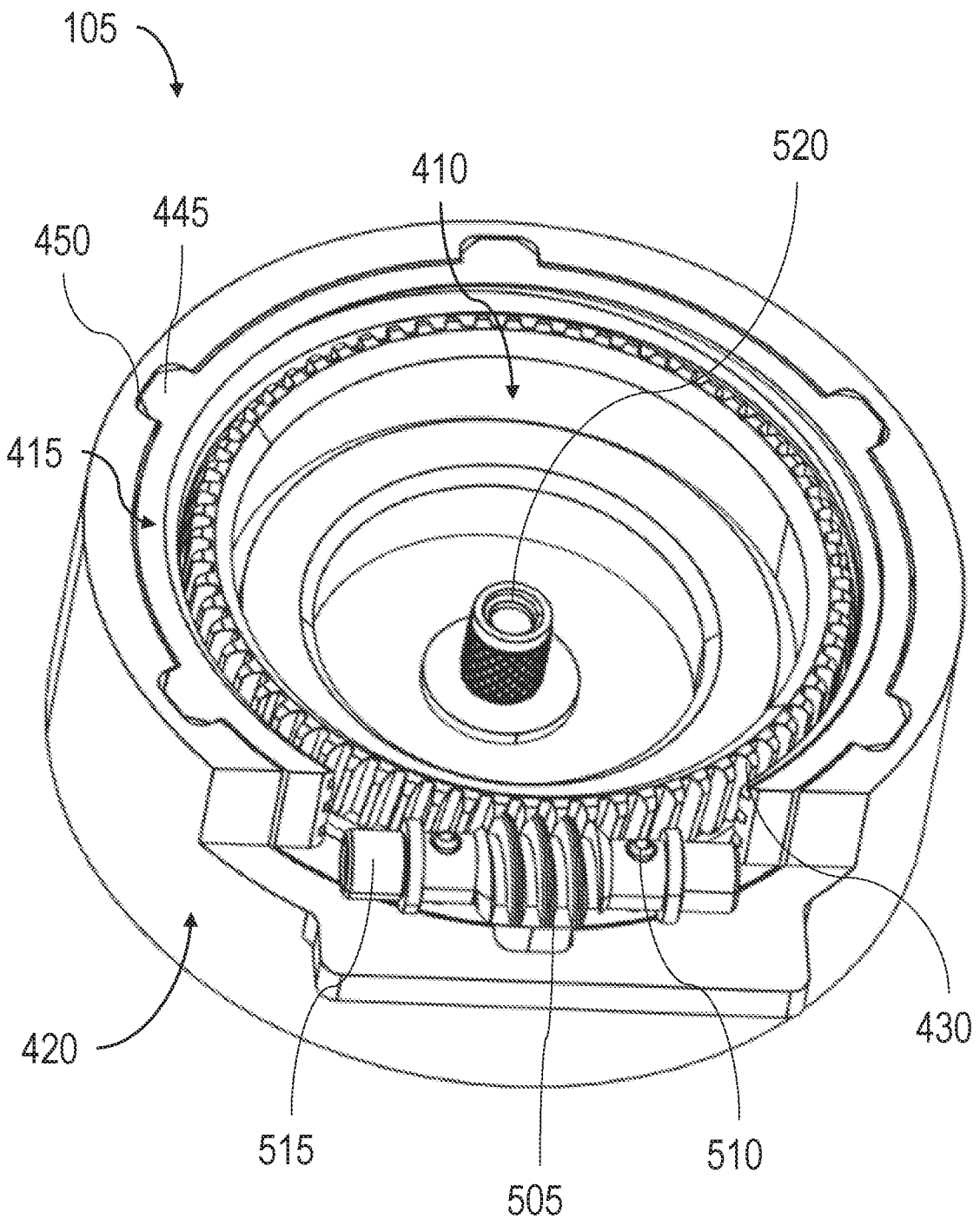
FIG. 5 is a top perspective view of a portion of the joint implant device of FIG. 1, in accordance with an implementation.

FIG. 5 illustrates an example of the first gear 505 engaging with the second gear 430. For example, FIG. 5 illustrates an example of an inner portion of body 105 (e.g., with the first support 405 removed). As shown in FIG. 5, and among others, the fourth support 420 can at least partially enclose the third support 415 such that the at least one alignment projection 445 can engage with a portion of the at least one alignment slot 450. The body 105 can include one or more components to facilitate engagement between the first gear 505 and the second gear 430. For example, the body 105 can include at least one gear fastener 510 that fastens the first gear 505 with the actuator 455 (not visible in FIG. 5). The body 105 can include at least one bushing 515 to facilitate rotation of the first gear 505 relative to the first support 405. For example, the body 105 can include two bushings 515 disposed on opposing sides of the first gear 505. The bushing 515 can engage with one or more portions of the first support 405 (e.g., within an aperture in the extension 425) to facilitate ease of rotation of the first gear 505.

In some examples, the joint implant device 100 can include at least one expandable insert 520, as shown in FIG. 5 and among others. For example, the expandable insert 520 can facilitate coupling one or more portions of the body 105 together. In some examples, the expandable insert 520 can include one or more threaded portions to facilitate coupling one or more portions of the body 105 together. The joint implant device 100 may include any number of expandable inserts 520. For example, the joint implant device 100 may not include any expandable inserts 520. The joint implant device 100 may include one expandable insert 520. The joint implant device 100 may include more than one expandable insert 520, as another example.

Figure 6:
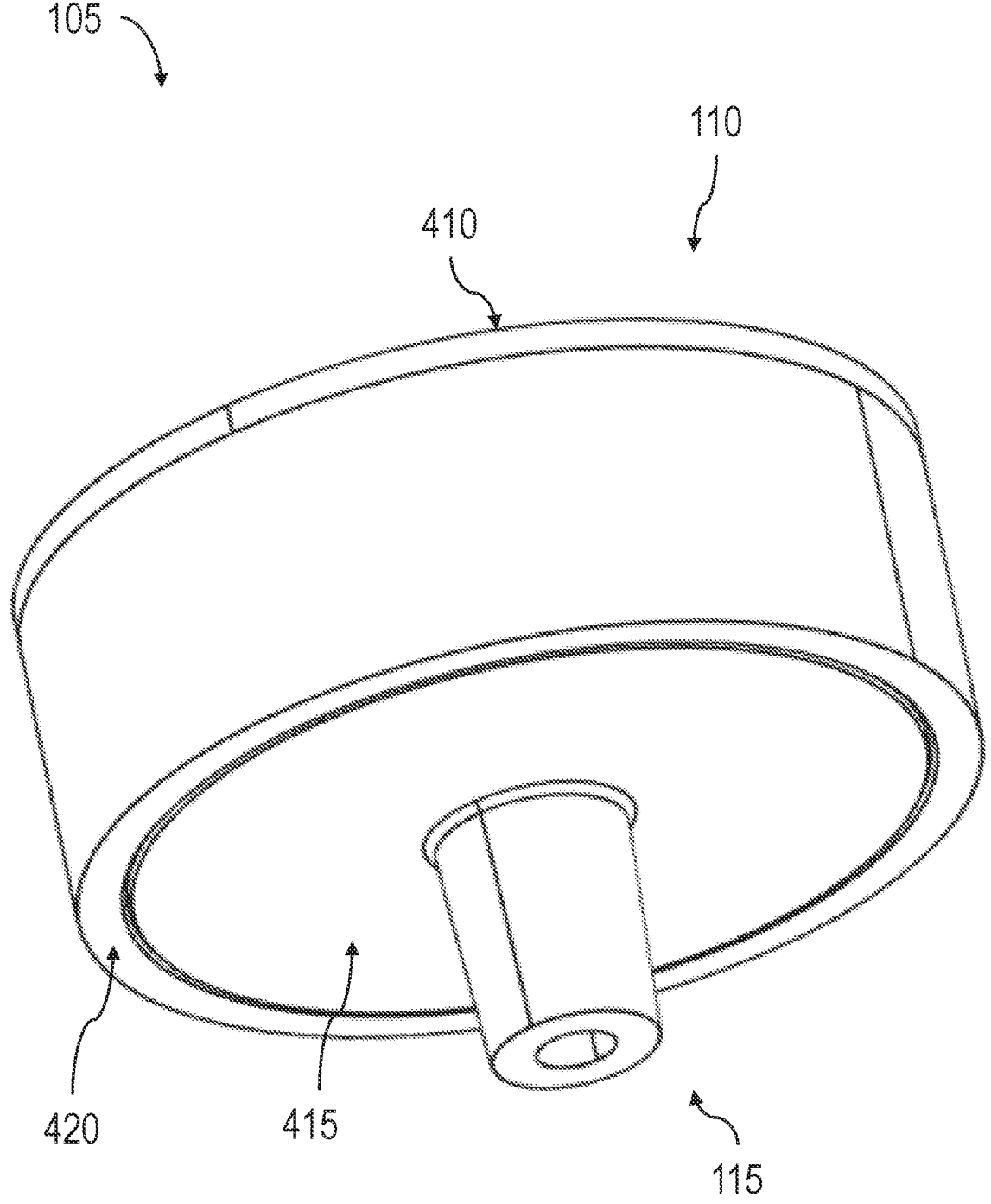
FIG. 6 is a bottom perspective view of a portion of the joint implant device of FIG. 1 in a first position, in accordance with an implementation.
Figure 7:
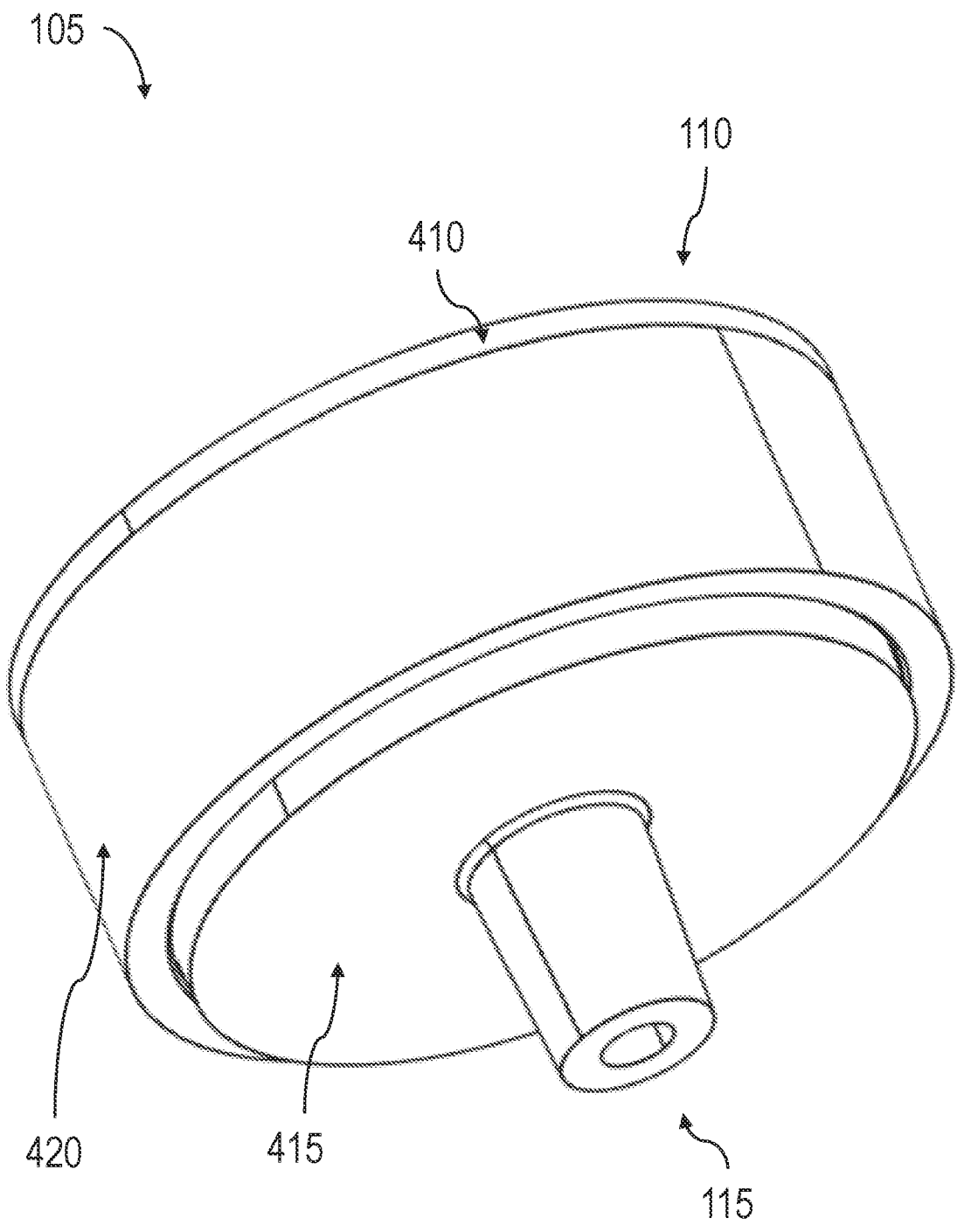
FIG. 7 is a bottom perspective view of a portion of the joint implant device of FIG. 1 in a second position, in accordance with an implementation.

FIG. 6 illustrates an example of the body 105 of the joint implant device 100 in a first position. For example, in the first position, the body 105 can have a minimum length (e.g., longitudinal extension between the first end 110 and the second end 115). In the first position, for example, at least one portion of the third support 415 may be flush with at least one portion of the fourth support 420. FIG. 7 illustrates an example of the body 105 of the joint implant device 100 in a second position. For example, in the second position, the body 105 can have a maximum length (e.g., longitudinal extension between the first end 110 and the second end 115). In the second position, for example, at least one portion of the third support 415 may be displaced a predetermined distance relative to the fourth support 420, as shown in FIG. 6. The third support 415 may extend beyond the fourth support 420 such that the overall length of the body 105 extends between the first position shown in at least FIG. 5 and the second position shown in FIG. 6. In some examples, the difference in length of the body 105 is about equal to (or slightly greater than) the difference in extension of the first plurality of corrugations 440 and the second plurality of corrugations 435 described above. For example, if the second plurality of corrugations 435 extends about 1 centimeter longitudinally between the first end 110 and the second end 115 of the body 105 along the second support 410 and the first plurality of corrugations 440 extends about 1.5 centimeters longitudinally between the first end 110 and the second end 115 of the body 105 along the third support 415, the length of the body 105 may extend about 0.5 centimeters between the first position and the second position. These examples are for illustrative purposes only.

The joint implant device 100 can include an adjustable length. For example, the body 105 of the joint implant device 100 can extend from a minimum length (e.g., such as the length of the body 105 in FIG. 6) to a maximum length (e.g., such as the length of the body 105 in FIG. 7). The joint implant device 100 can adjust 0 to 5 centimeters in length. For example, the third support 415 can move up to 5 centimeters relative to the first support 405 such that the axial length of the body 105 (e.g., extending longitudinally between the first end 110 and the second end 115) can extend up to 5 centimeters in length from an initial (e.g., minimum) position. In some examples, the joint implant device 100 can adjust between a range of 0% to 50% greater than the length of the body 105 in an initial position. For example, if the length of the body 105 is about 1 centimeter from the first end 110 to the second end 115 in an initial position, the body 105 may extend up to 1.5 centimeters in length in a final position. If the length of the body 105 is about 10 centimeters from the first end 110 to the second end 115 in an initial position, the body 105 may extend up to 15 centimeters in length in a final position. These examples are for illustrative purposes only and are not intended to limit the scope of the device 100. The device 100 can include various other lengths significantly smaller or larger than the provided illustrative examples.

The joint implant device 100 can include a continuous or incrementally adjustable length. For example, the body 105 of the joint implant device 100 can extend from a minimum length to a maximum length in continuously such that the body 105 includes a plurality of possible lengths (e.g., positions of the third support 415 relative to the first support 405) between the minimum length and the maximum length. In some examples, every 360° rotation of the second gear 430 can increase the length of the body 105 by the pitch of thread of the second support 410 (e.g., the pitch of one corrugation of the plurality of corrugations 435). The body 105 can adjust to various different lengths (e.g., continuous adjustment between a minimum length and a maximum length) to accommodate a desired length requirement, as described in greater detail below.

Figure 8:
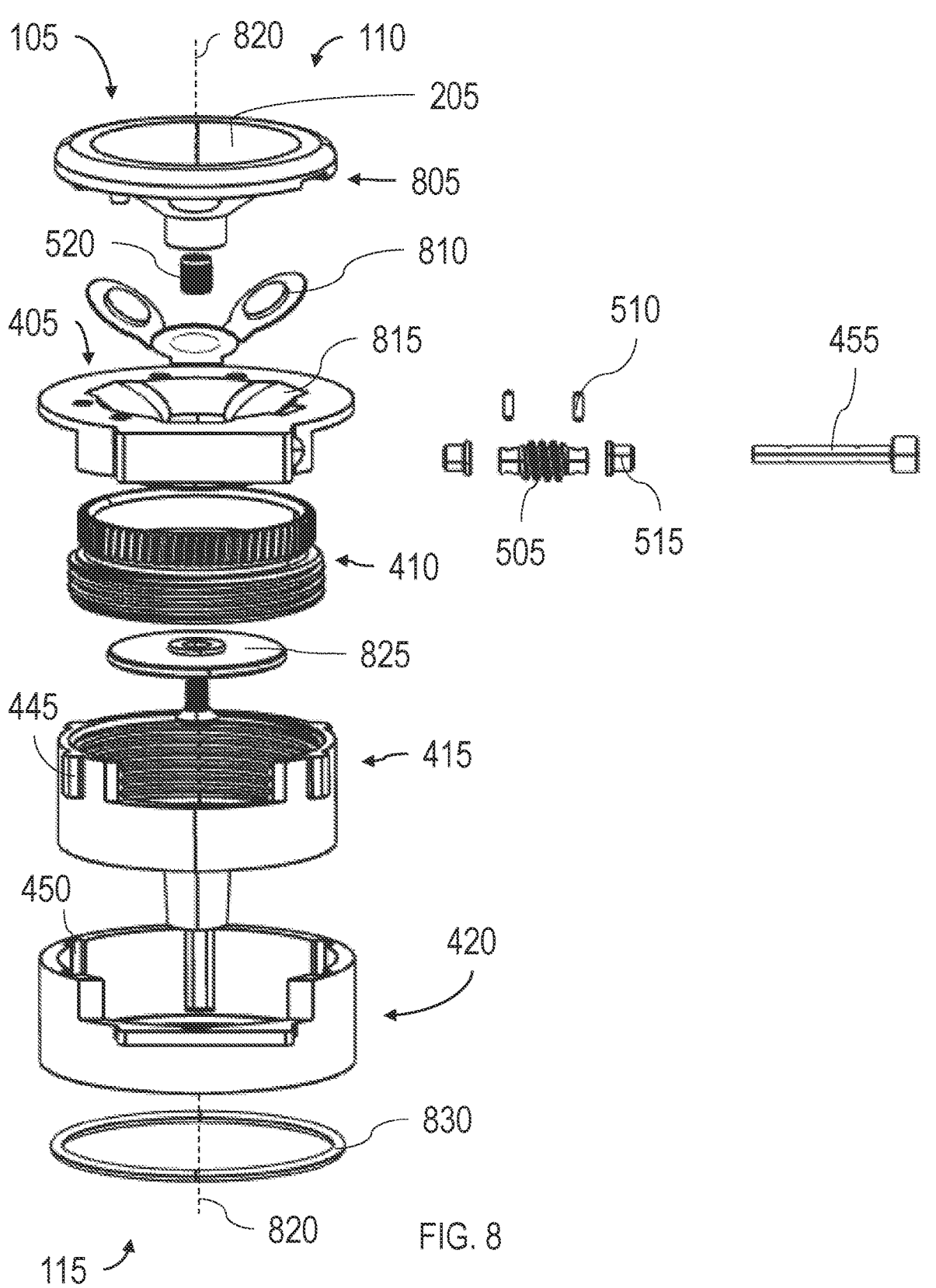
FIG. 8 is an exploded perspective view of a portion of the joint implant device of FIG. 1, in accordance with an implementation.

FIG. 8 illustrates a detailed exploded view of an example of the body 105 of the implant device 100. For example, FIG. 8 illustrates the body 105 exploded longitudinally about a central axis 820 of the body 105 extending between the first end 110 and the second end 115. As shown in FIG. 8, and among others, the joint implant device 100 can include a guide surface 805 coupled with the first support 405. In some examples, the guide surface 805 can be used for either an onlay joint implant device 100 or an inlay joint implant device 100. For example, the guide surface 805 can include various shapes, surfaces, or other components to couple with one or more components of a joint. In some examples, the guide surface 805 can include the annular surface 205 to receive a portion of the first joint component. The guide surface 805 can be the outermost portion of the body 105 at the first end 110. For example, the guide surface 805 can be an exterior surface of the body 105 to receive a portion of the first joint component. In some examples, the guide surface 805 can couple with one or more portions of the body 105 including the first support 405, the second support 410, the third support 415, or the fourth support 420. In some examples, the guide surface 805 abuts (e.g., rests against) one or more portions of the body 105, such as the first support 405.

The joint implant device 100 can include at least one washer 825. For example, the washer 825 can include a washer, a bearing, a bushing, or the like. For example, as shown in FIG. 8 and among others, the washer 825 can be disposed in a center portion of the body 105, such as between the second support 410 and the third support 415. In some examples, the washer 825 can couple with a portion of the third support 415 to facilitate ease of relative rotation between the second support 410 and the third support 415. The washer 825 can be any type of bearing, washer, or bushing. Alternatively or additionally, the joint implant device 100 can include at least one bushing positioned near or around the washer 825. For example, the bushing can be disposed near the washer 825 to further facilitate ease of relative rotation between one or more components of the body 105, such as between the second support 410 and the third support 415.

The joint implant device 100 can include at least one seal 830. For example, the seal 830 can be positioned between an outer portion of the third support 415 and an inner portion of the fourth support 420 such that the seal 830 is disposed between the third support 415 and the fourth support 420 to facilitate preventing fluid from flowing between the third support 415 and the fourth support 420. In some examples, an inner surface of the fourth support 420 can include a cannel, opening, aperture, or the like for the seal 830 to couple to the body 105 between the fourth support 420 and the third support 415. In some examples, the seal 830 is a gasket, such as an O-ring. The seal 830 can include various materials including, but not limited to, rubber or metal. The seal 830 can vary in shape or size to facilitate coupling to the body 105 to prevent fluid from flowing between the plurality of supports of the body 105, such as the third support 415 and the fourth support 420. In some examples, the joint implant device 100 can include a plurality of seals 830 disposed in various positions of the body 105. For example, at least one seal 830 may be positioned between a portion of the actuator 455 and a portion of the body 105, such as the first support 405. At least one seal 830 may be positioned between a portion of the guide surface 805 and the first support 405, as another example.

The joint implant device 100 can detect various metrics, parameters, or characteristics. For example, the joint implant device 100 can include at least one component to detect a physical metric of the joint implant device 100 occurring proximate the first end 110 of the body 105, such as a load force (e.g., amplitude and direction), pressure, stability, or other similar physical metrics. For example, the joint implant device can include at least one sensor 810 positioned near the first end 110 of the body 105, such as between the guide surface 805 and the first support 405. As shown throughout the figures, the sensor 810 can couple to a portion of the first support 405 between the first support 405 and the guide surface 805. In some examples, the first support 405 can include one or more divots 815 disposed on a surface of the first support 405 to receive a portion of the sensor 810.

The sensor 810 can detect a load force placed on the first end 110 of the body 105. For example, the sensor 810 can detect a load force from the first joint component placed upon the first end 110 of the body 105, such as on the annular surface 205 of the guide surface 805. In some examples, the sensor 810 can be placed just beneath the annular surface 205 such that the sensor 810 can detect one or more forces, pressures, or other similar points of contact disposed on the annular surface 205. The sensor 810 can be various types of sensors including, but not limited to, resistive sensors. For example, the sensor 810 can detect or measure a temperature, pressure, displacement, force, vibration, or the like occurring on or about the annular surface 205. In some examples, the sensor 810 can detect a physical metric of the joint implant device 100 based on a change in voltage or resistance of the sensor 810. For example, the sensor 810 can be an accelerometer, gyroscope, geomagnetic sensor, potentiometer, resistive position transducer, resistive pressure transducer, thermistor, strain gauge, or the like.

In some examples, the joint implant device 100 can include at least three sensors 810, as shown throughout the figures. For example, the three sensors 810 can each couple to the first support 405. In some examples, each of the three sensors 810 can couple to a different portion of the first support 405 such that the sensors 810 are circumferentially positioned about the central axis 820 of the body 105 of the joint implant device 100, as shown throughout the figures. In some examples, each sensor 810 is spaced an equal distance apart from one another circumferentially surrounding the central axis 820 of the body 105. For example, three sensors 810 can circumferentially surround an annular portion (e.g., adjacent or beneath the annular surface 205) of the first support 405 to facilitate detecting an amplitude and direction of a load force placed on a portion of the first end 110 of the body 105. In some examples, the joint implant device 100 can include more or less sensors 810. In some examples, each sensor 810 may be identical or symmetrically placed about the joint implant device 100, as shown throughout the figures. In some examples, each sensor 810 may be different or unsymmetrical about the joint implant device 100.

In some examples, the sensors 810 can detect, map, or otherwise determine a location of a load force (e.g., point of contact, orientation) on the joint implant device 100. For example, three sensors 810 can align with a center of rotation between the annular surface 205 of the joint implant device 100 and the first joint component (e.g., between a ball and socket joint). Each of the three sensors 810 can, for example, detect a vector direction and amplitude of the load force at each of the three locations of the sensors 810 disposed along a portion of the joint implant device 100. For example, each sensor 810 can detect a force relative to an axis of the sensor 810 (e.g., normal to the sensor 810). The sum (e.g., summation) of vector forces detected by each sensor 810 provides a total load force on the joint implant device 100, as described in greater detail below.

In some examples, the joint implant device 100 can include an internal module 1055 coupled with the joint implant device 100, as described in greater detail below. For example, the internal module 1055 can include various printed circuit boards (PCBs), wires, or other similar components that communicably couple with the one or more sensors 810. In some examples, the internal module 1055 is passive (e.g., does not include a power source directly attached to the internal module). In some examples, the internal module and the sensors 810 can couple through various wires, cables, pins, or by direct contact. In some examples, the internal module 1055 and the sensors 810 can couple through one or more wireless access points (e.g., via an antenna, Wi-Fi access point, etc.)

The joint implant device 100 can include an antenna. For example, the joint implant device 100 can include an antenna embedded within a portion of the body 105 of the joint implant device. In some examples, the antenna may couple to a center portion of the body 105 such that the antenna is not exposed to an exterior of the body 105. In some examples, the antenna may couple to an outer portion of the body 105, such as an outer surface of the fourth support 420. For example, the antenna (e.g., a PCB antenna) may circumferentially surround one or more portions of the fourth support 420 (e.g., spiral around, wrap around). In some examples, the antenna may integrally form with the fourth support 420 during or after manufacturing of the fourth support. For example, the antenna may be casted inside a portion of the fourth support 420.

The antenna may communicably couple to a portion of the one or more sensors 810. In some examples, the antenna may communicably couple with the internal module. In some examples, the antenna may communicably couple to the one or more sensors to wirelessly couple the sensors 810 with an external module separate from the joint implant device 100, as described in greater detail below. For example, the external module may include a patch, reinforcement, or the like to adhere to a portion of a patient's body (e.g., stick to the skin).

Figure 9:
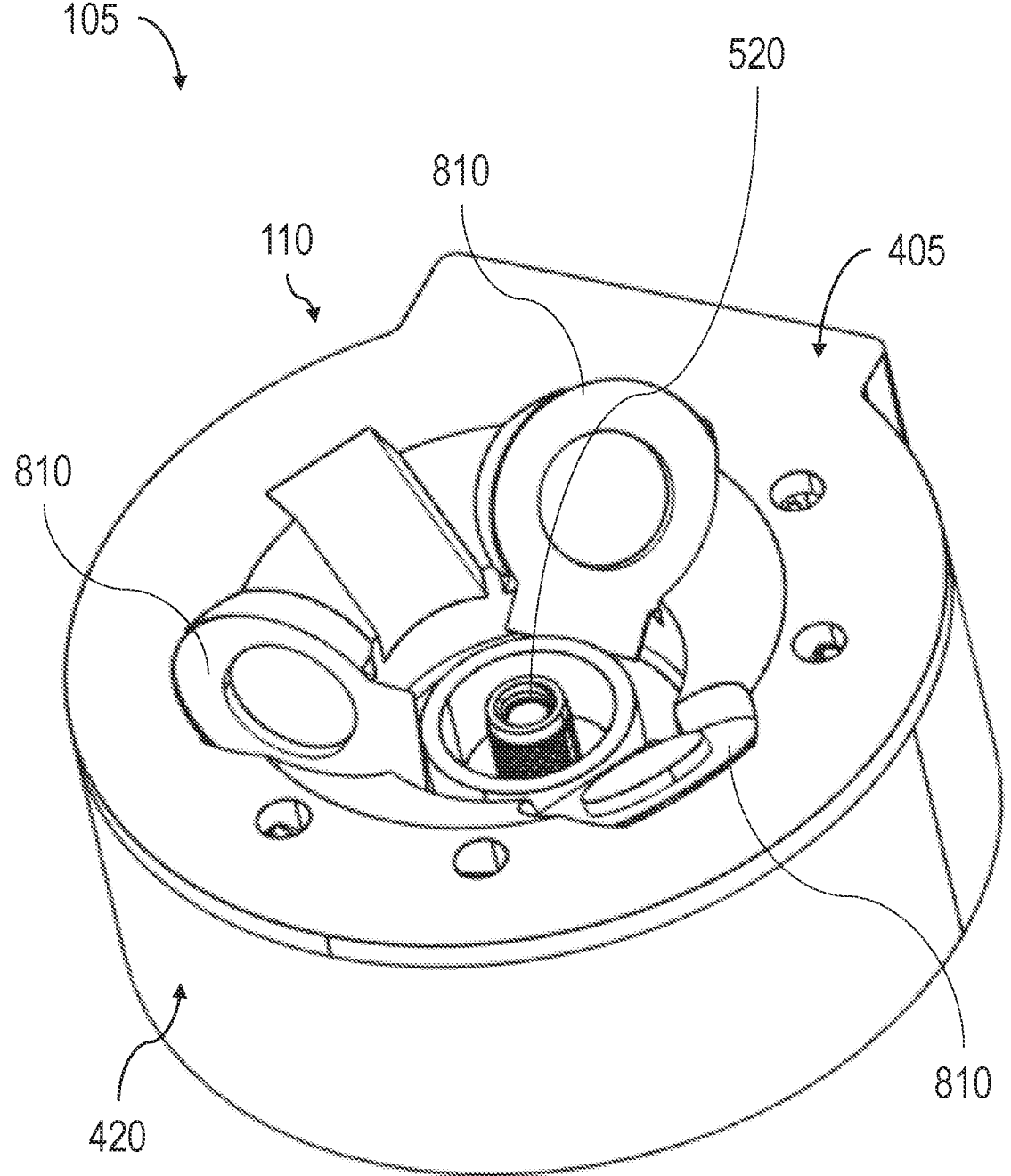
FIG. 9 is a top perspective view of a portion of the joint implant device of FIG. 1, in accordance with an implementation.

FIG. 9 illustrates a perspective top view of an example of the body 105. FIG. 9 illustrates, for example, an example positioning of the sensors 810 coupled with the first support 405. As shown in FIG. 9, and among others, the sensors 810 can couple to a portion of the first support 405 such that at least one portion of the sensor is disposed adjacent or slightly spaced apart from the annular surface (e.g., beneath the annular surface in view of the first end 110 of the device 100).

Figure 10:
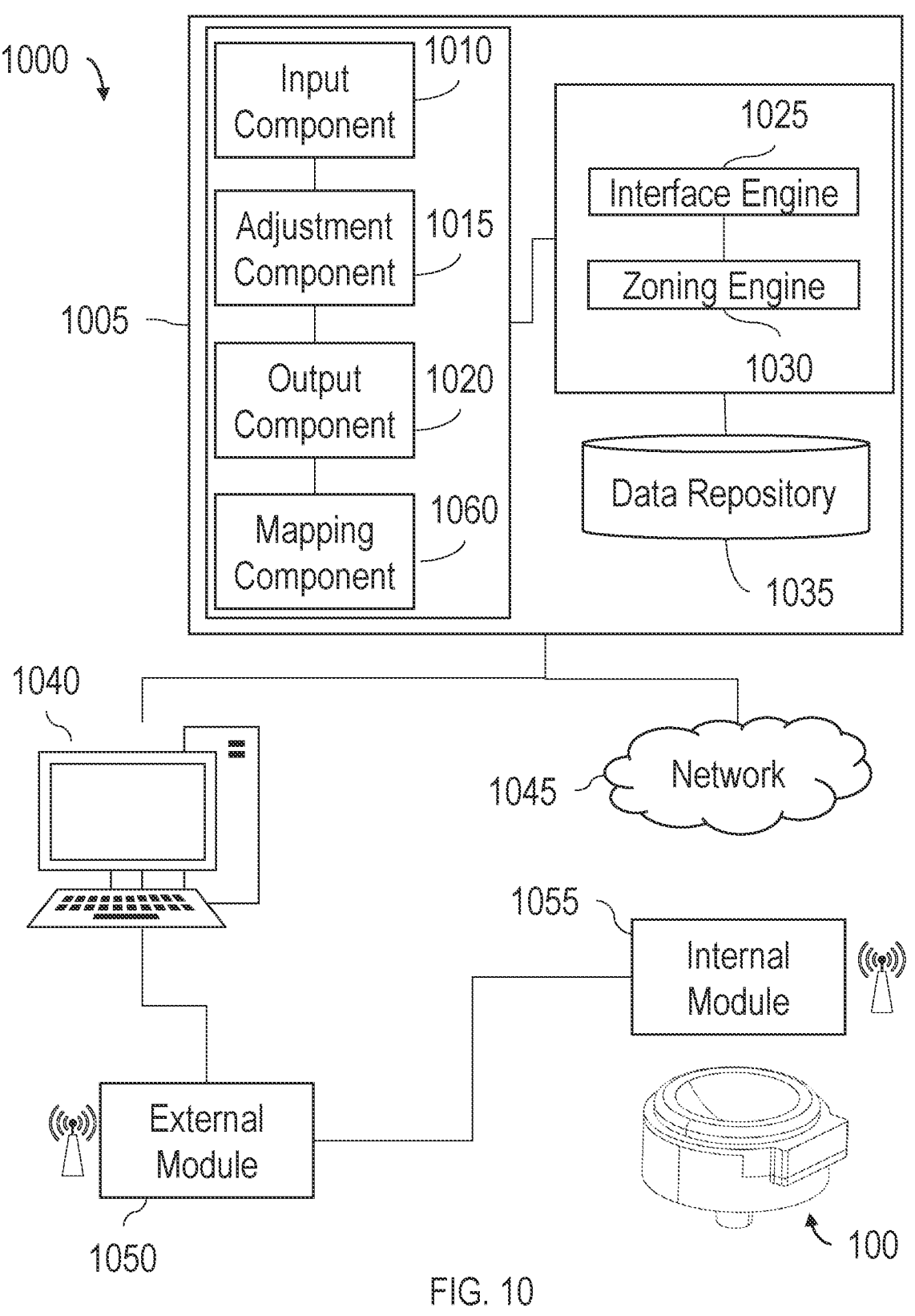
FIG. 10 is a schematic example of a joint implant device system, in accordance with an implementation.

FIG. 10 illustrates an example of a joint device system 1000. For example, the joint device system 1000 can facilitate evaluating the joint implant device 100. As described in greater detail below, the joint device system 1000 can include the joint implant device 100 and the internal module 1055. For example, the internal module 1055 can include the one or more sensors 810 described above. The internal module 1055 can receive at least one signal (e.g., data packet, an indication, etc.) from another portion of the joint device system 1000, such as an external module 1050. For example, the external module 1050 can transmit a signal to the internal module 1055. In some examples, the external module 1050 can include one or more transceivers, phased array radar systems, or transmitters to transmit a signal from the external module 1050 to the internal module 1055. In some examples, the external module 1050 can include one or more frequency generators such that the external module 1050 can transmit radio frequency signals (e.g., oscillations, electromagnetic waves, vibrations, etc.) in multiple directions. For example, the radio signals can reflect off of or be absorbed by one or more components of the joint implant device 100 to create a radio frequency feedback loop between the external module 1050 and the internal module 1055. In some examples, one or more signals, such as radio frequency signals, can cause the first gear 505 to rotate, as described in greater detail below.

One or more components of the internal module 1055 can receive the one or more signals from the external module 1050. For example, the antenna integrally formed with the joint implant device 100 can receive the signal. In some examples, the external module 1050 can transmit a signal to the antenna such that the antenna and the external module 1050 cause the internal module 1055 (e.g., the sensors 810 and the PCB) to activate (e.g., turn on or off).

As described above, the sensors 810 can detect a load on the joint implant device 100. In some examples, the electrical properties of the sensors 810 can change or fluctuate when a load is placed on the joint implant device 100. The internal module 1055 can detect a change or fluctuation of the sensors 810 and can adjust or change one or more properties of a radio frequency loop between the external module 1050 and the internal module 1055, which can create a change in a reflected signal from the internal module 1055 to the external module 1050.

The external module 1050 can receive a signal (e.g., data packet, an indication, etc.) from the internal module 1055. For example, the external module 1050 can receive a reflected radio frequency signal from the internal module 1055 in response to the transmitted signal from the external module 1050. The external module 1050 can be separate from the joint implant device 100. For example, the external module 1050 can be physically positioned apart from the joint implant device 100.

In some examples, the external module 1050 can analyze the signal from the internal module 1055 and determine, based on the analyzed signal, data corresponding to the load force on the joint implant device. In some examples, the external module 1050 can communicably couple to one or more computing devices to transmit the data corresponding to the load force, the position of the body 105 (e.g., within a joint), or orientation in space of the joint implant device 100.

The joint device system 1000 can include at least one data processing system 1005. The data processing system 1005 can include a variety of different components including, but not limited to, an input component 1010, an adjustment component 1015, an output component 1020, and a mapping component 1060. The data processing system 1005 can include several engines including, but not limited to, an interface engine 1025 and a zoning engine 1030. The data processing system 1005 can include at least one database, such as a data repository 1035. While these components and engines are shown in FIG. 10, the data processing system 1005 may include any number of device evaluating components or engines, including additional components or engines which may be incorporated into, supplement, or replace one or more of the engines shown in FIG. 10.

The data processing system 1005 can include several components or engines. For example, the data processing system 1005 can include components or engines to transmit or receive data from one or more remote sources (such as the computing devices, the external module 1050, or the internal module 1055). In some examples, communications device(s) may access the network 1045 to exchange data with various other communications device(s) via cellular access, a modem, broadband, Wi-Fi, satellite access, etc. via the data processing system 1005. The data processing system 1005 may be any device(s), component(s), circuit(s), or other combination of hardware components designed or implemented to receive inputs or other signals for evaluating the joint implant device 100. For example, the data processing system 1005 can receive inputs or other signals for evaluating the joint implant device 100 when the device 100 is being used within a joint, such as a shoulder joint.

The data processing system 1005 can communicably couple with at least one client computing device 1040. The data processing system 1005 may communicably couple with the client computing device 1040 via a communications link or network 1045 (which may be or include various network connections configured to communicate, transmit, receive, or otherwise exchange data between addresses corresponding to the client computing device 1040 and data processing system 1005). The network 1045 may be a Local Area Network (LAN), a Wide Area Network (WAN), a Wireless Local Area Network (WLAN), an Internet Area Network (IAN) or cloud-based network, etc. The network 1045 may facilitate communication between the respective components of the joint device system 1000, as described in greater detail below.

The input component 1010 of the data processing system 1005 can obtain data based on the signal from the internal module 1055 to the external module 1050. For example, the input component 1010 can obtain data transmitted from the external module 1050 corresponding to a load force on the joint implant device 100. In some examples, the data transmitted from the external module 1050 may include one or more voltage measurements detected by each sensor 810. For example, the input component 1010 can calibrate each sensor (e.g., based on one or more calibration curves using one or more known loads) and can determine, based on the calibration, a corresponding force value for each detected voltage of each sensor 810 individually or simultaneously.

The adjustment component 1015 can determine an indication to adjust the joint implant device 100. For example, the adjustment component 1015 can evaluate the data obtained by the input component 1010 and can determine if the data corresponds to a stable tension force on the joint implant device 100. In some examples, the adjustment component 1015 may determine, based on the signal received by the external module 1050, that the joint implant device 100 includes too large of a force (e.g., has too much tension). For example, if a desired tension force of the joint implant device 100 (e.g., between the first joint component and the annular surface 205) is about 20 N and a detected force measurement greater than 500 N, the adjustment component 1015 may determine that an adjustment of the joint implant device 100 is required. In some examples, this adjustment corresponds to a change in length of the body 105 of the joint implant device 100 as described above. This example is for illustrative purposes only and is not limiting to the scope of the joint implant device 100. The desired load force or the force at which the adjustment component 1015 determines an indication to adjust the joint implant device 100 may occur at various other force measurements.

In some examples, the adjustment component 1015 can determine an indication to adjust the first gear 505 of the joint implant device 100. For example, the adjustment component 1015 can determine an indication to adjust the length of the body 105 of the joint implant device 100, which may indicate that an adjustment to the first gear 505 of the device 100 is needed. In some examples, one or more tools can detect or localize a position of an interface of the first gear 505, such as an interface of the actuator 455, to adjust the first gear 505. For example, an arthroscopy can detect a location of an interface of the actuator 455 such that a user can locate and adjust the first gear 505 with the actuator 455 (e.g., using a hand tool via a minimally invasive procedure). In some examples, the adjustment component 1015 can transmit one or more signals to the joint implant device 100 (e.g., via the external module 1050 or internal module 1055) to cause rotation of the first gear 505. For example, the adjustment component 1015 can cause the joint implant device 100 to automatically adjust based on an indication to adjust the device 100. In some examples, the adjustment component 1015 can cause the joint implant device 100 to automatically adjust such that no surgical procedure is necessary to adjust the joint implant device 100 (e.g., via a non-invasive procedure). In some examples, the input component 1010 can receive an input (e.g., a user input) from a computing device, such as a computer or mobile device, to adjust the joint implant device 100. For example, the adjustment component 1015 can cause the joint implant device 100 to automatically adjust based on a user input on a mobile device application. In some examples, the data processing system 1005 can include or can communicably couple with one or more AI systems to facilitate automatically adjusting the joint implant device 100.

In some examples, the adjustment component 1015 can determine an indication to maintain the joint implant device 100 in a position. For example, the external module 1050 may receive a signal from the internal module 1055 that indicates a stable force upon the joint implant device 100. By way of non-limiting example, if a desired tension force of the joint implant device 100 is about 20 N and a detected force measurement is about 20 N, the adjustment component 1015 may determine that no adjustment of the joint implant device 100 is required. This example is for illustrative purposes only and is not limiting to the scope of the joint implant device 100. The desired load force or the force at which the adjustment component 1015 determines an indication not to adjust the joint implant device 100 may occur at various other force measurements.

In some examples, the adjustment component 1015 can determine an indication to adjust or maintain the joint implant device 100 based on a location of the load force of the joint implant device 100. For example, the mapping component 1060 can map a location of the load force of the joint implant device 100 on a portion of the annular surface 205 of the joint implant device 100, as described above in reference to FIG. 8. The adjustment component 1015 can determine, based on the detected location of a sum of forces detected by each sensor 810, whether to adjust or maintain the joint implant device 100. For example, if a detected location of the force on the annular surface 205 is far away from a center point of the surface 205 (e.g., far away from central axis 820, about 50% or more of the radius of the annular surface 205 away from the central axis 820), the adjustment component 1015 may determine an indication to adjust the joint implant device 100. If a detected location of the force on the annular surface 205 is near the center point of the surface 205, the adjustment component 1015 may determine an indication to maintain the position of the joint implant device (e.g., not extend/retract the length of the body 105). This example is for illustrative purposes only and is not limiting to the scope of the joint implant device 100.

In some examples, the adjustment component 1015 may determine a tension force (e.g., a soft-tissue tension force) that needs to be applied to set the joint implant device 100 (e.g., specifically for each patient). For example, the adjustment component 1015 can detect a load force (amplitude and direction) and determine an increase or decrease of the load force (e.g., by adjusting the length of the body 105) required to reach a desired load force. In some examples, the adjustment component 1015 can determine a tension force applied to the joint implant device 100 to optimize a lifetime of the joint implant device 100. For example, the adjustment component 1015 can determine a tension or compression force applied to the joint implant device 100 to limit fatigue, stress, or other factors to optimize use of the joint implant device 100 as long as possible (e.g., reduce fracture, breakage, or other damage of the device 100).

Figure 11:
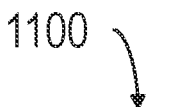
FIG. 11 is a schematic of a portion of the system of FIG. 10, in accordance with an implementation.
Figure 11:
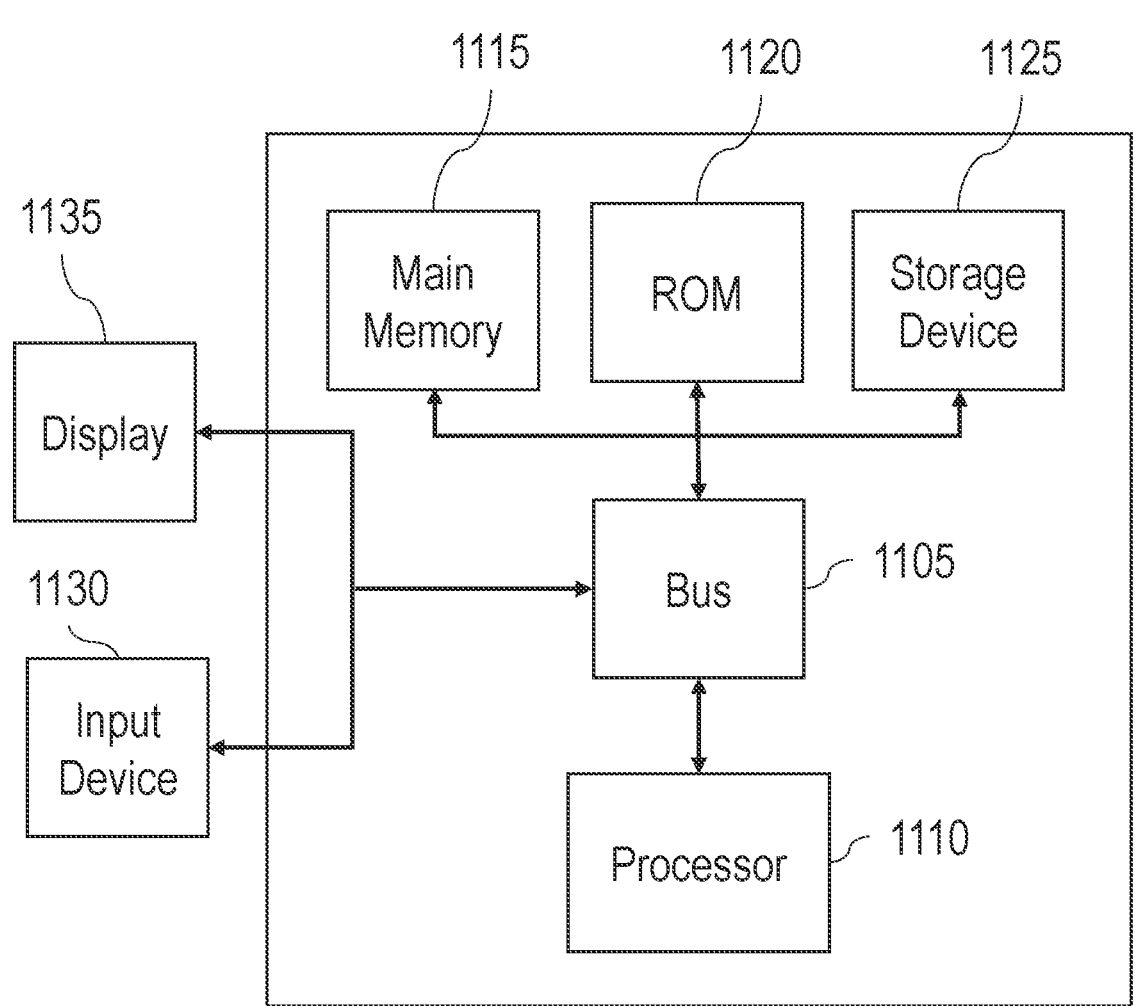

FIG. 11 illustrates a block diagram of an example computer system 1100. The computer system or computing device 1100 can include or be used to implement the system 1000, or its components such as the data processing system 1005. The computing system 1100 includes a bus 1105 or other communication component for communicating information and a processor 1110 or processing circuit coupled to the bus 1105 for processing information. The computing system 1100 can also include one or more processors 1110 or processing circuits coupled to the bus for processing information. The computing system 1100 also includes main memory 1115, such as a random access memory (RAM) or other dynamic storage device, coupled to the bus 1105 for storing information, and instructions to be executed by the processor 1110. The main memory 1115 can be or include a data repository. The main memory 1115 can also be used for storing position information, temporary variables, or other intermediate information during execution of instructions by the processor 1110. The computing system 1100 may further include a read only memory (ROM) 1120 or other static storage device coupled to the bus 1105 for storing static information and instructions for the processor 1110. A storage device 1125, such as a solid state device, magnetic disk or optical disk, can be coupled to the bus 1105 to persistently store information and instructions. The storage device 1125 can include or be part of the data repository.

The computing system 1100 may be coupled via the bus 1105 to a display 1135, such as a liquid crystal display, or active matrix display, for displaying information to a user. An input device 1130, such as a keyboard including alphanumeric and other keys, may be coupled to the bus 1105 for communicating information and command selections to the processor 1110. The input device 1130 can include a touch screen display 1135. The input device 1130 can also include a cursor control, such as a mouse, a trackball, or cursor direction keys, for communicating direction information and command selections to the processor 1110 and for controlling cursor movement on the display 1135. The display 1135 can be part of the data processing system 1005, the client computing device 1040 or other component of FIG. 10, for example.

The processes, systems and methods described herein can be implemented by the computing system 1100 in response to the processor 1110 executing an arrangement of instructions contained in main memory 1115. Such instructions can be read into main memory 1115 from another computer-readable medium, such as the storage device 1125. Execution of the arrangement of instructions contained in main memory 1115 causes the computing system 1100 to perform the illustrative processes described herein. One or more processors in a multi-processing arrangement may also be employed to execute the instructions contained in main memory 1115. Hard-wired circuitry can be used in place of or in combination with software instructions together with the systems and methods described herein. Systems and methods described herein are not limited to any specific combination of hardware circuitry and software.

Although an example computing system has been described in FIG. 11, the subject matter including the operations described in this specification can be implemented in other types of digital electronic circuitry, or in computer software, firmware, or hardware, including the structures disclosed in this specification and their structural equivalents, or in combinations of one or more of them.

Figure 12:
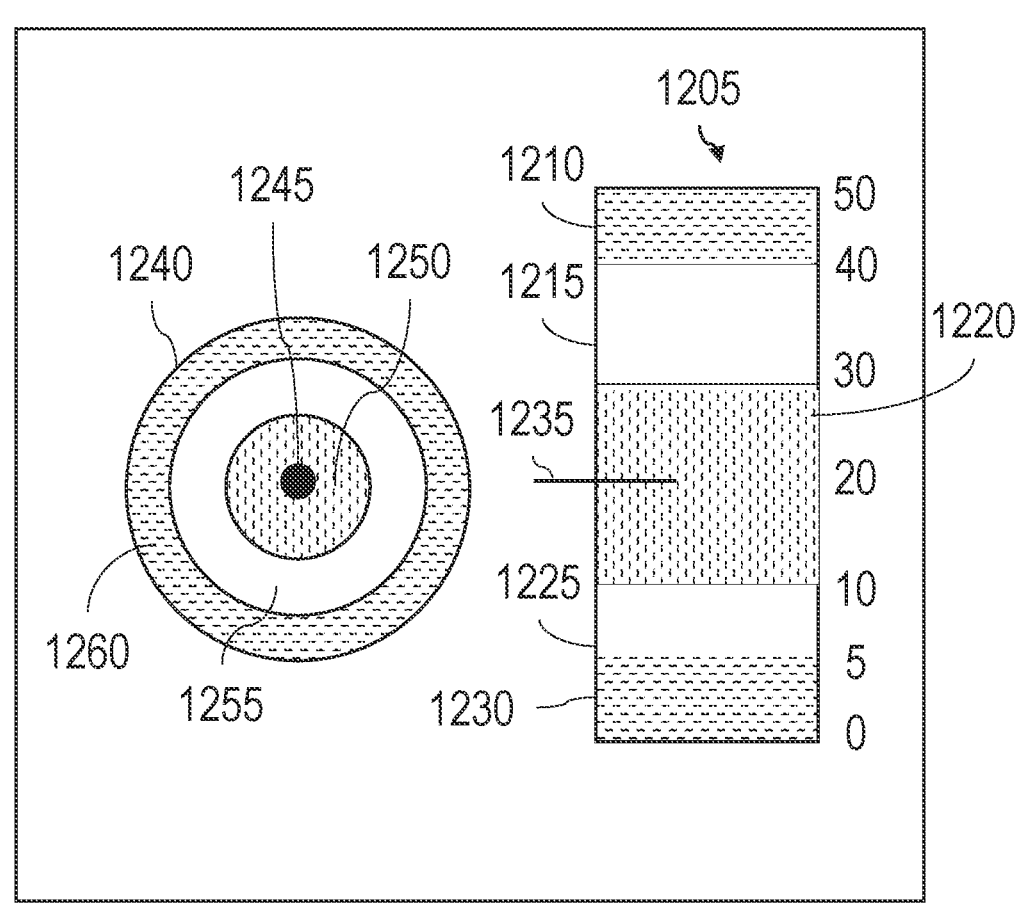
FIG. 12 is an example of a graphical user interface, in accordance with an implementation.
Figure 13:
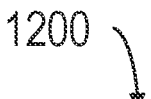
FIG. 13 is an example of a graphical user interface, in accordance with an implementation.
Figure 13:
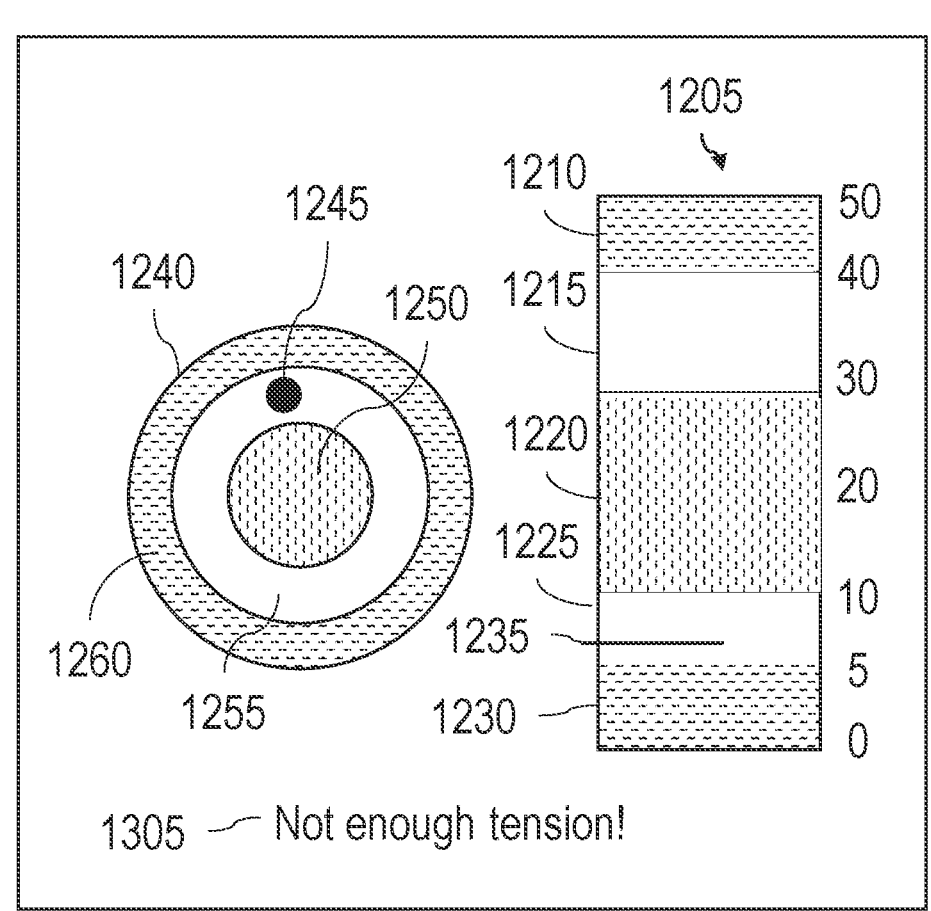

The output component 1020 can render the indication to adjust the joint implant device 100. For example, the output component 1020 can operably or communicably couple with the interface engine 1025 or the zoning engine 1030 to graphically render the indication to adjust the joint implant device 100 on a user interface. For example, FIGS. 12 and 13 illustrate an example of a graphical user interface 1200. FIGS. 12 and 13 illustrate one example of a rendered graphical user interface 1200 from the output component 1020 of the data processing system 1005, for example. The output component 1020 can render the graphical user interface 1200 on any computing device including, but not limited to, a computer, tablet, or mobile device. In some examples, the data processing system 1005 can communicably couple to one or more computing devices, such as a mobile device, such that the data processing system 1005 can render the graphical user interface 1200 through a mobile device application on the mobile device. The output component 1020 can render a graphical representation of a load force on the joint implant device 100 detected from the sensor 810. For example, the output component 1020 can graphically render the graphical representation of the load force on the joint implant device 100 on a graphical user interface. As shown in FIGS. 12 and 13, the graphical user interface 1200 can include a scale 1205. For example, the scale 1205 can include a graphical representation of the load force on the joint implant device 100.

The output component 1020 can render a graphical representation of the load force on the joint implant device 100 that includes at least two distinct zones based on a predetermined range of the load force. The scale 1205 can include a plurality of zones. For example, the zoning engine 1030 can cause the output component 1020 to render the scale 1205 including a first zone 1210, a second zone 1215, and a third zone 1220. The graphical user interface 1200 may include one or more features to signal that the load force measurement detected by the sensors 810 has reached a zone. For example, the graphical user interface 1200 may include a zone indicator 1235 (e.g., a line, marker, arrow) that moves between each zone, as shown in FIGS. 12 and 13.

The first zone 1210, the second zone 1215, and the third zone 1220 can include at least one visible or audible distinction to differentiate between the zones. For example, the first zone 1210 may be a first color or pattern (e.g., red), the second zone 1215 may be a second color or pattern (e.g., yellow), and the third zone may be a fourth color or pattern (e.g., green). In some examples, each zone may be associated with a corresponding noise or sound. For example, the output component 1020 can render a unique sound for each zone when the zone indicator 1235 approaches or enters (e.g., when the detected force falls within the range of the zone) the respective zone.

In some examples, the first zone 1210 may correspond to a first threshold range of the load force on the joint implant device 100. For example, the first zone 1210 may correspond to an amplitude of load force well outside of (e.g., much greater than) a normal range. In some examples, the first zone 1210 may correspond to too much soft tissue tension, which can facilitate identifying an increased risk of fracture of the device 100. In some examples, the first zone 1210 may correspond to an amplitude of load force that is greater than or equal to about 30% more than a normal load force. For example, if a desired load force on the joint implant device 100 is about 20 N, then a force equal to or greater than 40 N may fall within the first zone 1210. The second zone 1215 may correspond to an amplitude of load force that is just outside of (e.g., greater than) a normal range. For example, if a desired load force on the joint implant device 100 is about 20 N, then a force equal to or greater than 30 N may fall within the second zone 1215. The third zone 1220 may correspond to an amplitude of load force that is within a normal range. In some examples, the third zone 1220 may correspond to an ideal patient specific soft tissue tension force. For example, if a desired load force on the joint implant device 100 is about 20 N, then a load force between 15 N and 25 N may fall within the third zone 1220. These examples are for illustrative purposes only. Other examples of the graphical user interface 1200 may include various other load force ranges at varying load forces.

In some examples, the scale 1205 can include a fourth zone 1225 and a fifth zone 1230. For example, the fourth zone 1225 may correspond to an amplitude of load force that is just outside of (e.g., less than) a normal range. For example, if a desired load force on the joint implant device 100 is about 20 N, then a force less than or equal to 10 N may fall within the fourth zone 1225. The fifth zone 1230 may correspond to an amplitude of load force well outside of (e.g., much less than) a normal range. In some examples, the fifth zone 1230 may correspond to too low of soft tissue tension, which can facilitate identifying an increased risk of instability of the device 100. The fifth zone 1230 may correspond to an amplitude of load force that is less than or equal to about 30% less than a normal load force. For example, if a desired load force on the joint implant device 100 is about 20 N, then a force less than or equal to 5 N may fall within the fifth zone 1230.

In some examples, the fourth zone 1225 may correspond to the second zone 1215. For example, the fourth zone 1225 and the second zone 1215 may have the same visual or audio indication (e.g., same color). In some examples, the fifth zone 1230 may correspond to the first zone 1210. For example, the fifth zone 1230 and the first zone 1210 may have the same visual or audio indication (e.g., same color).

The graphical user interface 1200 can include a load force stability representation 1240. In some examples, the stability representation 1240 may represent or resemble a portion of the joint implant device 100, such as the annular surface 205. The stability representation 1240 may represent a stability or a location (e.g., a bearing point 1245) of the load force or sum of load forces acting on the joint implant device 100. In some examples, the stability representation 1240 can include one or more zones. For example, the stability representation 1240 may include a first zone 1250, a second zone 1255, or a third zone 1260. For example, the first zone 1250 may represent a stable force, the second zone 1255 may represent a force just outside of a stable force (e.g., mid-stable), and the third zone 1260 may represent an unstable force. In some examples, each zone of the stability representation 1240 may include one or more colors, sounds, or other similar indicators of the zone.

The output component 1020 can present a notification 1305 based on the predetermined range of the load force on the joint implant device 100. For example, as the zone indicator 1235 moves from a "normal" zone (e.g., about a desired tension force), such as the third zone 1220 to an "abnormal" zone (e.g., not a desired tension force), such as the fourth zone 1225, the output component 1020 can present the notification 1305 on the user interface 1200 to indicate an adjustment of the joint implant device 100 is required. The notification 1305 illustrated in FIG. 13 is meant for illustrative purposes only and is not limited to the scope of the present technical solution. The notification 1305 can include various other symbols, texts, sounds, numbers, or the like to indicate that an adjustment is needed.

The output component 1020 can present a recommended dimension of the joint implant device 100. For example, the output component 1020 can present a recommended length of the body 105 based on the indication to adjust the joint implant device 100. In some examples, the output component 1020 can present the recommended dimension through the notification 1305 on the user interface 1200. In some examples, the output component 1020 can present a recommended change in length of the body 105 of the joint implant device 100 based on the indication to adjust the joint implant device 100. In some examples, the adjustment component 1015 can determine a recommended dimension of the joint implant device 100 that offers optimized patient outcomes (e.g., comfort of patient using device 100 within their joint, for example). In some examples, the output component 1020 can present a graphical representation of a load force of the joint implant device 100 against one or more voltage measurements detected by the one or more sensors 810. For example, the output component 1020 can render a graphical representation (e.g., a graph) displaying a voltage measurement against a detected force of the joint implant device 100.

Figure 14:
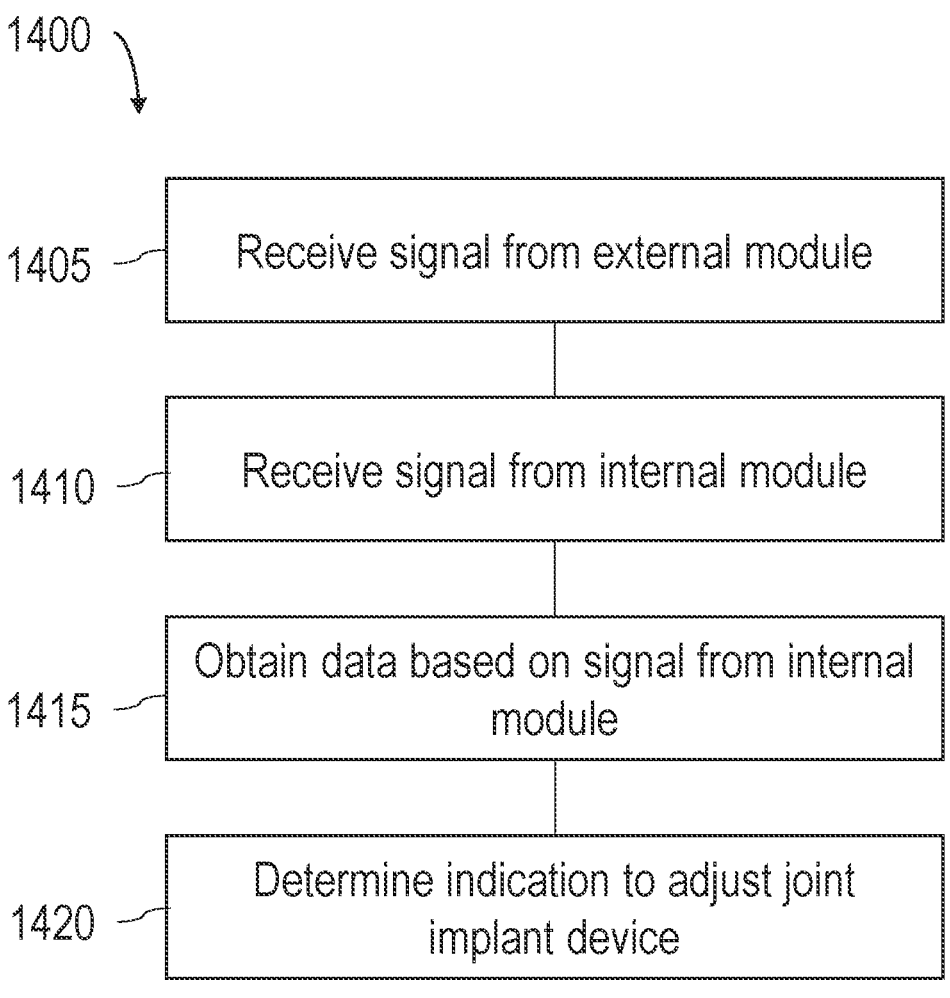
FIG. 14 is an illustration of an example of a method for evaluating a joint implant device, in accordance with an implementation.

FIG. 14 illustrates an example of a method 1400 of evaluation a joint implant device 100. The method 1400 can include receiving a signal from the external module 1050, as depicted in act 1405. For example, the internal module 1055 of the joint implant device 100 can receive the signal. In some examples, the internal module 1055 of the joint implant device 100 can receive the signal from the external module 1050 to activate the joint implant device 100 (e.g., activate the sensors 810, power the internal module 1055, etc.). As described in greater detail above, one or more portions of the joint implant device 100, such as the internal module 1055, can reflect the signal away from the joint implant device 100, such as towards the external module 1050.

The method 1400 can include receiving a signal from the internal module 1055, as depicted in act 1410. For example, the external module 1050 can receive the signal from the internal module 1055. In some examples, the external module 1050 can receive a reflected frequency signal from the internal module 1055 in response to a first frequency signal from the external module 1050 to the internal module 1055. In some examples, the reflected signal corresponds to a detected load or movement of the first end 110 of the joint implant device 100.

The method 1400 can include obtaining data based on the signal received from the internal module 1055, as depicted in act 1415. For example, the input component 1010 of the data processing system 1005 can obtain one or more data, or inputs, from the external module 1050 based on the reflected signal from the internal module 1055. In some examples, the data corresponds to a detected load on the first end 110 of the joint implant device 100. For example, the input component 1010 may obtain one or more voltage or resistance measurements of the sensors 810 corresponding to a change in load on the first end 110 of the joint implant device 100.

The method 1400 can include determining an indication to adjust the joint implant device 100, as depicted in act 1420. For example, one or more components of the data processing system 1005, such as the adjustment component 1015, can determine whether an adjustment of the length of the body 105 of the joint implant device 100 is required. For example, if a tension force of the joint implant device 100 is too high (e.g., greater than 10% more than a desired force, for example), the adjustment component 1015 can determine an indication to adjust the length of the body 105 of the joint implant device 100. If a tension force of the joint implant device 100 is too low (e.g., less than 10% less than a desired force, for example), the adjustment component 1015 can determine an indication to adjust the length of the body 105 of the joint implant device 100. In some examples, the first gear 505 can adjust based on the indication to adjust the length of the body 105. For example, a user can adjust the length of the body 105 of the joint implant device 100 by causing the first gear 505 to rotate (e.g., by using a hand tool). As described in greater detail above, the rotation of the first gear 505 can cause the length of the body 105 to extend or retract.

In some examples, the adjustment component 1015 can determine to maintain the joint implant device 100 in a position. For example, if a detected tension force on the first end 110 of the joint implant device 100 is about equal to a desired tension force (e.g., within 10% of the desired force, for example), the adjustment component 1015 can determine that an adjustment to the length of the body 105 is not required.

The computing system(s) described herein can include clients and servers. A client and server are generally remote from each other and typically interact through a communication network. The relationship of client and server arises by virtue of computer programs running on the respective computers and having a client-server relationship to each other. In some implementations, a server transmits data (e.g., data packets) to a client device (e.g., for purposes of displaying data to or receiving user input from a user interacting with the client device). Data generated at the client device (e.g., a result of the user interaction) can be received from the client device at the server.

The separation of various system components does not require separation in all implementations, and the described program components can be included in a single hardware or software product. For example, the components described herein can be a single component, app, or program, or a logic device having one or more processing circuits, or executed by one or more processors of the data processing system(s).

Some of the description herein emphasizes the structural independence of the aspects of the system components. Other groupings or components that execute similar overall operations are understood to be within the scope of the present application. Modules or components can be implemented in hardware or as computer instructions on a non-transient computer readable storage medium, and modules can be distributed across various hardware or computer based components.

The systems described above can provide multiple ones of any or each of those components and these components can be provided on either a standalone system or on multiple instantiation in a distributed system. In addition, the systems and methods described above can be provided as one or more computer-readable programs or executable instructions embodied on or in one or more articles of manufacture. The article of manufacture can be cloud storage, a hard disk, a CD-ROM, a flash memory card, a PROM, a RAM, a ROM, or a magnetic tape. In general, the computer-readable programs can be implemented in any programming language, such as LISP, PERL, C, C++, C#, PROLOG, or in any byte code language such as JAVA. The software programs or executable instructions can be stored on or in one or more articles of manufacture as object code.

Example and non-limiting module implementation elements include sensors providing any value determined herein, sensors providing any value that is a precursor to a value determined herein, datalink or network hardware including communication chips, oscillating crystals, communication links, cables, twisted pair wiring, coaxial wiring, shielded wiring, transmitters, receivers, or transceivers, logic circuits, hard-wired logic circuits, reconfigurable logic circuits in a particular non-transient state configured according to the module specification, any actuator including at least an electrical, hydraulic, or pneumatic actuator, a solenoid, an op-amp, analog control elements (springs, filters, integrators, adders, dividers, gain elements), or digital control elements.

The subject matter and the operations described herein can be implemented in digital electronic circuitry, or in computer software, firmware, or hardware, including the structures disclosed in this specification and their structural equivalents, or in combinations of one or more of them. The subject matter described herein can be implemented as one or more computer programs, e.g., one or more circuits of computer program instructions, encoded on one or more computer storage media for execution by, or to control the operation of, data processing apparatuses. The program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. While a computer storage medium is not a propagated signal, a computer storage medium can be a source or destination of computer program instructions encoded in an artificially generated propagated signal. The computer storage medium can also be, or be included in, one or more separate components or media (e.g., multiple CDs, disks, or other storage devices include cloud storage). The operations described in this specification can be implemented as operations performed by a data processing apparatus on data stored on one or more computer-readable storage devices or received from other sources.

The terms "computing device", "component" or "data processing apparatus" or the like encompass various apparatuses, devices, and machines for processing data, including by way of example a programmable processor, a computer, a system on a chip, or multiple ones, or combinations of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, app, script, or code) can be written in any form of programming language, including compiled or interpreted languages, declarative or procedural languages, and can be deployed in any form, including as a stand-alone program or as a module, component, subroutine, object, or other unit suitable for use in a computing environment. A computer program can correspond to a file in a file system. A computer program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatuses can also be implemented as, special purpose logic circuitry, e.g., an FPGA (field programmable gate array) or an ASIC (application specific integrated circuit). Devices suitable for storing computer program instructions and data can include non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

The subject matter described herein can be implemented in a computing system that includes a back end component, e.g., as a data server, or that includes a middleware component, e.g., an application server, or that includes a front end component, e.g., a client computer having a graphical user interface or a web browser through which a user can interact with an implementation of the subject matter described in this specification, or a combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

While operations are depicted in the drawings in a particular order, such operations are not required to be performed in the particular order shown or in sequential order, and all illustrated operations are not required to be performed. Actions described herein can be performed in a different order.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements and features discussed in connection with one implementation are not intended to be excluded from a similar role in other implementations.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation or embodiment, and references to "an implementation," "some implementations," "one implementation" or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

References to "or" may be construed as inclusive so that any terms described using "or" may indicate any of a single, more than one, and all of the described terms. References to at least one of a conjunctive list of terms may be construed as an inclusive OR to indicate any of a single, more than one, and all of the described terms. For example, a reference to "at least one of 'A' and 'B'" can include only 'A', only 'B', as well as both 'A' and 'B'. Such references used in conjunction with "comprising" or other open terminology can include additional items.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

Modifications of described elements and acts such as variations in sizes, dimensions, structures, shapes and proportions of the various elements, values of parameters, mounting arrangements, use of materials, colors, orientations can occur without materially departing from the teachings and advantages of the subject matter disclosed herein. For example, elements shown as integrally formed can be constructed of multiple parts or elements, the position of elements can be reversed or otherwise varied, and the nature or number of discrete elements or positions can be altered or varied. Other substitutions, modifications, changes and omissions can also be made in the design, operating conditions and arrangement of the disclosed elements and operations without departing from the scope of the present disclosure.

Systems and methods described herein may be embodied in other specific forms without departing from the characteristics thereof. For example, the joint implant device 100 can be implanted in a shoulder joint, a knee joint, an ankle joint, or a hip joint. Further relative parallel, perpendicular, vertical or other positioning or orientation descriptions include variations within +/−10% or +/−10 degrees of pure vertical, parallel or perpendicular positioning. References to "approximately," "about" "substantially" or other terms of degree include variations of +/−10% from the given measurement, unit, or range unless explicitly indicated otherwise. Coupled elements can be electrically, mechanically, or physically coupled with one another directly or with intervening elements. Scope of the systems and methods described herein is thus indicated by the appended claims, rather than the foregoing description, and changes that come within the meaning and range of equivalency of the claims are embraced therein.

What is claimed is:

1. A joint implant device, comprising:
   a prosthesis body having a first end to couple with a first joint component and a second end to couple with a second joint component, the prosthesis body comprising:
   a first support;
   a first gear rotatably coupled with the first support, the first gear to rotate with the first support in a stationary position relative to a rotation direction;
   a second support movably coupled with the first support, the second support having a second gear to engage with a portion of the first gear;
   a third support movably coupled with the second support, the third support including a projection that extends in an axial direction along an outer surface of the third support;

a fourth support including a slot that extends in the axial direction along an inner surface of the fourth support, the slot configured to receive the projection of the third support to rotatably fix the fourth support to the third support; and the third support to move in the axial direction relative to the first support and the fourth support with activation of the first gear to elongate the prosthesis body.

2. The joint implant device of claim 1, comprising:

the second support including a plurality of corrugations threadably engaged with a corresponding plurality of corrugations positioned on the third support.

3. The joint implant device of claim 1, comprising:

a guide surface coupled with the first support, the guide surface having an annular portion to at least partially receive the first joint component.

4. The joint implant device of claim 1, comprising:

the fourth support configured to at least partially enclose the third support.

5. The joint implant device of claim 1, comprising:

a sensor coupled with the first support of the prosthesis body, the sensor to detect a load force placed on the first end of the prosthesis body.

6. The joint implant device of claim 5, comprising:

a second sensor and a third sensor each coupled with the first support of the prosthesis body; and the sensor, the second sensor, and the third sensor, each positioned circumferentially around an annular portion of the first support.

7. The joint implant device of claim 6, comprising:

the sensor, the second sensor, and the third sensor each spaced an equal distance apart from one another about a center axis of the prosthesis body.

8. The joint implant device of claim 5, comprising:

an antenna coupled with the prosthesis body and communicably coupled with the sensor and an external module.

9. The joint implant device of claim 5, wherein the sensor is configured to detect an orientation and a magnitude of the load force and a position and orientation of the prosthesis body.

10. The joint implant device of claim 1, comprising:

a bearing disposed between the second support and the third support, the bearing configured to facilitate movement of the third support relative to the first support.

11. The joint implant device of claim 1, comprising:

an actuator operably coupled with the first gear, the actuator including at least one portion exposed to an exterior of the prosthesis body to receive a portion of a user tool.

12. The joint implant device of claim 1, comprising:

a seal coupled with the prosthesis body, the seal to facilitate preventing fluid from entering an internal portion of the prosthesis body.

13. The joint implant device of claim 1, wherein the third support is configured to move up to 3 centimeters relative to the first support such that a total length of the prosthesis body can increase up to 3 centimeters.

14. A joint implant device, comprising:

a body having a first end to couple with a sphere and a second end to couple with a stem;

a sensor coupled with the body, the sensor to detect a physical metric proximate the first end of the body;

the body comprising:

a guide surface;

a first support coupled with the guide surface;

a worm gear rotatably coupled with the first support, the worm gear to rotate with the first support in a stationary position relative to a rotation direction;

a second support movably coupled with the first support, the second support having a worm wheel to engage with the worm gear;

a third support movably coupled with the second support, the third support including a projection that extends in an axial direction along an outer surface of the third support;

a fourth support including a slot that extends in the axial direction along an inner surface of the fourth support, the slot configured to receive the projection of the third support to rotatably fix the fourth support to the third support; and the third support to move in the axial direction up to 5 centimeters relative to the first support and the fourth support with activation of the worm wheel to elongate the body.

15. The joint implant device of claim 14, wherein the physical metric is a load force, and the sensor is configured to detect the load force upon the first end of the body.

16. The joint implant device of claim 14, comprising:

an antenna coupled with the body, the antenna to facilitate transmitting the physical metric detected from the sensor to an external module.

17. The joint implant device of claim 14, comprising:

the second support including a plurality of corrugations threadably engaged with a corresponding plurality of corrugations of the third support.

18. The joint implant device of claim 14, comprising:

the guide surface having an annular portion to at least partially receive the sphere.

19. The joint implant device of claim 14, comprising:

a second sensor and a third sensor each coupled with the body;

the physical metric is a load force; and the sensor, the second sensor, and the third sensor to detect the load force disposed on the first end of the body.

20. The joint implant device of claim 19, comprising:

the sensor, the second sensor, and the third sensor, each spaced circumferentially around an annular portion of the first support.

\* \* \* \* \*